United States Patent
Edick et al.

(10) Patent No.: US 10,589,005 B2
(45) Date of Patent: Mar. 17, 2020

(54) BIOERODIBLE MAGNESIUM ALLOY MICROSTRUCTURES FOR ENDOPROSTHESES

(71) Applicant: Boston Scientific Scimed, Inc., Maple Grove, MN (US)

(72) Inventors: Jacob Drew Edick, Minneapolis, MN (US); Jonathan S. Stinson, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 137 days.

(21) Appl. No.: 15/068,132

(22) Filed: Mar. 11, 2016

(65) Prior Publication Data

US 2016/0263288 A1    Sep. 15, 2016

Related U.S. Application Data

(60) Provisional application No. 62/131,554, filed on Mar. 11, 2015.

(51) Int. Cl.
*A61L 31/02* (2006.01)
*A61L 31/14* (2006.01)
(Continued)

(52) U.S. Cl.
CPC .............. *A61L 31/022* (2013.01); *A61F 2/04* (2013.01); *A61F 2/06* (2013.01); *A61F 2/82* (2013.01);
(Continued)

(58) Field of Classification Search
CPC ...... A61F 2/82; A61F 2/04; A61F 2/06; A61F 2/844; A61F 2/852; A61F 2/856;
(Continued)

(56) References Cited

U.S. PATENT DOCUMENTS

| 4,542,539 A | 9/1985 | Rowe, Jr. et al. |
| 5,073,207 A | 12/1991 | Faure et al. |

(Continued)

FOREIGN PATENT DOCUMENTS

| CN | 105142687 | 12/2015 |
| EP | 1548138 | 6/2005 |

(Continued)

OTHER PUBLICATIONS

"International Preliminary Report on Patentability," for PCT Application No. PCT/US2016/022110 dated Sep. 21, 2017 (10 pages).
(Continued)

*Primary Examiner* — Katherine H Schwiker
(74) *Attorney, Agent, or Firm* — Pauly, DeVries Smith & Deffner LLC

(57) ABSTRACT

A bioerodible endoprosthesis includes a bioerodible body including an alloy comprising at least 85 weight percent magnesium and at least one high-melting-temperature element having a melting temperature of greater than 700° C. The alloy has a microstructure including equiaxed magnesium-rich phase grains and optionally high-melting-temperature intermetallic phases. The equiaxed magnesium-rich phase grains have an average grain diameter of less than or equal to 10 microns. High-melting-temperature intermetallic phases, if present, can have an average longest dimension of 3 microns or less.

14 Claims, 10 Drawing Sheets

(51) Int. Cl.
*A61F 2/04* (2013.01)
*A61F 2/06* (2013.01)
*A61F 2/82* (2013.01)
*B21C 23/00* (2006.01)
*C22C 23/02* (2006.01)
*C22C 23/06* (2006.01)

(52) U.S. Cl.
CPC .......... *A61L 31/148* (2013.01); *B21C 23/002* (2013.01); *C22C 23/02* (2013.01); *C22C 23/06* (2013.01); *A61F 2240/001* (2013.01)

(58) Field of Classification Search
CPC .... A61F 2/86; A61F 2/88; A61F 2/885; A61F 2/90; A61F 2/91; A61F 2/915; A61F 2/9293; A61F 2/966; A61F 2/89; A61F 2/848; A61F 2/2418; A61F 2002/821; A61F 2002/823; A61F 2002/825; A61F 2002/826; A61F 2002/91508; A61F 2002/91516; A61F 2002/91525; A61F 2002/91533; A61F 2002/91541; A61F 2002/9155; A61F 2002/91558; A61F 2002/91566; A61F 2002/91575; A61F 2002/91583; A61F 2002/91591; A61F 2210/0004; A61F 2250/003; A61L 31/148; A61L 31/022
USPC ........................................................ 623/138
See application file for complete search history.

(56) References Cited

U.S. PATENT DOCUMENTS

| | | | |
|---|---|---|---|
| 5,516,522 A | 5/1996 | Peyman et al. | |
| 5,769,884 A | 6/1998 | Solovay | |
| 5,843,172 A | 12/1998 | Yan | |
| 6,240,616 B1 | 6/2001 | Yan | |
| 6,287,332 B1 | 9/2001 | Bolz et al. | |
| 6,290,721 B1 | 9/2001 | Heath et al. | |
| 6,521,061 B1 | 2/2003 | Fukunaga et al. | |
| 6,686,053 B2* | 2/2004 | Wada | C22C 21/02 428/472.2 |
| 6,716,444 B1 | 4/2004 | Castro et al. | |
| 6,723,120 B2 | 4/2004 | Yan et al. | |
| 6,770,086 B1 | 8/2004 | Girton | |
| 6,908,516 B2* | 6/2005 | Hehmann | C23C 14/14 148/406 |
| 6,953,560 B1 | 10/2005 | Castro et al. | |
| 8,052,744 B2 | 11/2011 | Girton et al. | |
| 8,202,477 B2 | 6/2012 | Papirov et al. | |
| 8,449,603 B2 | 5/2013 | Weber et al. | |
| 8,840,660 B2 | 9/2014 | Weber | |
| 9,522,220 B2 | 12/2016 | Edick | |
| 9,603,728 B2 | 3/2017 | Stinson et al. | |
| 2002/0004060 A1 | 1/2002 | Heublein et al. | |
| 2002/0197178 A1 | 12/2002 | Yan et al. | |
| 2004/0039438 A1 | 2/2004 | Alt et al. | |
| 2004/0220660 A1 | 11/2004 | Shanley et al. | |
| 2004/0267354 A1 | 12/2004 | Ringeisen et al. | |
| 2005/0119723 A1 | 6/2005 | Peacock et al. | |
| 2005/0192657 A1 | 9/2005 | Colen et al. | |
| 2005/0261760 A1 | 11/2005 | Weber et al. | |
| 2005/0283229 A1 | 12/2005 | Dugan et al. | |
| 2006/0122694 A1* | 6/2006 | Stinson | A61F 2/91 623/1.34 |
| 2006/0193886 A1 | 8/2006 | Owens et al. | |
| 2006/0199876 A1 | 9/2006 | Troczynski et al. | |
| 2006/0229711 A1 | 10/2006 | Yan et al. | |
| 2006/0271168 A1 | 11/2006 | Kleine et al. | |
| 2007/0264303 A1 | 11/2007 | Atanasoska et al. | |
| 2007/0281073 A1 | 12/2007 | Gale et al. | |
| 2008/0004691 A1 | 1/2008 | Weber et al. | |
| 2008/0031765 A1* | 2/2008 | Gerold | C22C 23/00 420/404 |
| 2008/0082162 A1 | 4/2008 | Boismier et al. | |
| 2008/0109072 A1 | 5/2008 | Girton et al. | |
| 2008/0195189 A1 | 8/2008 | Asgari et al. | |
| 2009/0081313 A1 | 3/2009 | Segal et al. | |
| 2009/0088834 A1 | 4/2009 | Wang | |
| 2009/0192595 A1 | 7/2009 | Kawamura et al. | |
| 2010/0161031 A1 | 6/2010 | Papirov et al. | |
| 2010/0262222 A1 | 10/2010 | Weber et al. | |
| 2011/0172724 A1 | 7/2011 | Hort et al. | |
| 2012/0046734 A1 | 2/2012 | Girton et al. | |
| 2012/0053674 A1 | 3/2012 | Boismier et al. | |
| 2012/0059455 A1 | 3/2012 | Weber et al. | |
| 2012/0095548 A1* | 4/2012 | Gregorich | A61L 27/04 623/1.46 |
| 2012/0215301 A1 | 8/2012 | Papirov et al. | |
| 2013/0039805 A1 | 2/2013 | Somekawa et al. | |
| 2013/0041455 A1 | 2/2013 | Gerold | |
| 2013/0090741 A1 | 4/2013 | Guo et al. | |
| 2013/0144290 A1* | 6/2013 | Schiffl | C22C 23/04 606/62 |
| 2013/0331927 A1* | 12/2013 | Zheng | A61F 2/82 623/1.19 |
| 2013/0333809 A1 | 12/2013 | Oishi et al. | |
| 2014/0200652 A1* | 7/2014 | Bayer | A61F 2/06 623/1.15 |
| 2014/0236284 A1 | 8/2014 | Stinson et al. | |
| 2014/0277372 A1* | 9/2014 | Ngo | A61F 2/82 623/1.15 |
| 2015/0066135 A1 | 3/2015 | Weber et al. | |
| 2015/0157767 A1 | 6/2015 | Edick | |
| 2016/0138148 A1* | 5/2016 | Schaffer | C22C 23/04 428/649 |
| 2017/0056562 A1 | 3/2017 | Edick | |
| 2017/0072112 A1 | 3/2017 | Stinson | |
| 2017/0106123 A1 | 4/2017 | Weber et al. | |

FOREIGN PATENT DOCUMENTS

| | | |
|---|---|---|
| EP | 2210625 | 7/2010 |
| EP | 2959925 | 12/2015 |
| EP | 2613817 | 3/2016 |
| EP | 3062832 | 9/2017 |
| EP | 2068964 | 11/2017 |
| JP | 2010121161 | 6/2010 |
| JP | 2016509875 | 4/2016 |
| WO | 2007082147 | 7/2007 |
| WO | 2008016150 | 2/2008 |
| WO | 2008034013 | 3/2008 |
| WO | 2008034066 | 3/2008 |
| WO | 2008036870 | 3/2008 |
| WO | 2008091835 | 7/2008 |
| WO | 2009036140 | 3/2009 |
| WO | 2009137786 | 11/2009 |
| WO | 2010003003 | 1/2010 |
| WO | 2010093244 | 8/2010 |
| WO | 2009152153 | 9/2010 |
| WO | 2010014612 | 10/2010 |
| WO | 2011011531 | 3/2011 |
| WO | 2010040084 | 6/2011 |
| WO | 2011081958 | 7/2011 |
| WO | 2011117298 | 9/2011 |
| WO | 2012003502 | 1/2012 |
| WO | 2012033637 | 3/2012 |
| WO | 2014001240 | 1/2014 |
| WO | 2014126958 | 8/2014 |
| WO | 2015066181 | 5/2015 |
| WO | 2016145368 | 9/2016 |

OTHER PUBLICATIONS

"Non-Final Office Action," for U.S. Appl. No. 15/392,547 dated Dec. 26, 2017 (24 pages).

"Office Action," for Japanese Patent Application No. 2015-558089 dated Oct. 17, 2017 (9 pages) with English translation.

"Response to Communication Pursuant to Article 94(3) EPC," for European Patent Application No. 15176192.1, filed with the EPO Jul. 17, 2017 (9 pages).

(56) References Cited

OTHER PUBLICATIONS

"Response to Communication Pursuant to Rules 161(1) and 162 EPC," for European Patent Application No. 16711107.9 filed with the EPO May 3, 2018 (10 pages).
"Response to Non-Final Office Action," for U.S. Appl. No. 15/392,547 filed with the USPTO Apr. 24, 2018 for NFOA dated Dec. 26, 2017 (8 pages).
"Communication Pursuant to Article 94(3) EPC," for European Patent Application No. 15176192.1, dated Mar. 27, 2017 (5 pages).
Erinc, M et al., "Applicability of Existing Magnesium Alloys as Biomedical Implant Materials," Proceedings of the Symposium held during the TMS Annual Meeting & Exhibition, San Francisco, CA, 2009, pp. 209-214.
Erinc, M. et al., "Modified AZ80 Magnesium Alloys for Biomedical Applications," Magnesium Technology, 2010, pp. 641-646.
"File History," for European Patent Application No. 11752046.0 downloaded from the EPO Jan. 24, 2017 (190 pages).
"File History," for U.S. Appl. No. 13/216,371.
George, S. M. et al., "Molecular Layer Deposition of Organic and Hybrid Organic-Inorganic Polymers," Material Matters, 2008 (3.2), p. 34-37.
"International Preliminary Report on Patentability," for PCT/US2011/048954 dated Mar. 12, 2013 (7 pages).
"International Search Report and Written Opinion," for PCT/US2011/048954 dated Oct. 19, 2011 (10 pages).
"Response to Communication Pursuant to Article 94(3) EPC," for European Patent Application No. 07842447.0 filed with the EPO Dec. 13, 2016 (52 pages).
"Second Office Action," for Chinese Patent Application No. 201480020886.4 dated Apr. 5, 2017 (6 pages).
Seman, Michael et al., "Self-Limiting Growth of Tantalum Oxide Thin Films by Pulsed Plasma-Enhanced Chemical Vapor Deposition," Applied Physics Letters, 2007, 90: 131504 (3 pages).
"Communication Pursuant to Article 94(3) EPC," for European Patent Application No. 07842447.0 dated Oct. 7, 2016 (4 pages).
"First Office Action," for Chinese Patent Application No. 201480020886.4 dated Oct. 8, 2016 (19 pages) with English Translation.
"Non-Final Office Action," for U.S. Appl. No. 14/178,869 dated Aug. 26, 2016 (22 pages).
"Response to Non-Final Office Action," for U.S. Appl. No. 14/178,869, dated Aug. 26, 2016 and filed with the USPTO Oct. 27, 2016 (8 pages).
Xu, Guang-Liang et al., "Effect of Equal Channel Angular Extrusion on the Microstructure and Mechanical Properties of AZ31 Magnesium Alloy," Material Engineering, vol. 2, Feb. 28, 2011, pp. 69-72.
Chakkedath, J. B. et al., "The Effect of Nd on the Tension and Compression Deformation Behavior of Extruded Mg-1Mn (wt pct) at Temperatures Between 298 K and 523 K (25 degrees C and 250 degrees C)," Metallurgical and Materials Transactions A, vol. 45A, Jul. 2014, pp. 3254-3274 (21 pages).
Cho, S. S. et al., "Structure and properties of rapidly solidified Mg—Al alloys," Journal of Materials Science 34,1999 (11 pages), 4311-4320.
"Communication Pursuant to Article 94(3) EPC," for European Patent Application No. 15176192.1, dated Nov. 25, 2015 (4 pages).
"Communication Pursuant to Rules 161(1) and 162 EPC," for European Patent Application No. 14706247.5, dated Oct. 30, 2015 (1 page).
"Final Office Action," for U.S. Appl. No. 13/284,467, dated Jan. 25, 2016 (16 pages).
"Final Office Action," for U.S. Appl. No. 14/178,869, dated Apr. 5, 2016 (16 pages).
"International Preliminary Report on Patentability," for PCT Application No. PCT/US2014/062902, dated May 12, 2016 (9 pages).
"International Preliminary Report on Patentability," for PCT/US2007/078417 dated Mar. 17, 2009 (7 pages).
"International Preliminary Report on Patentability," for PCT/US2009/046750 dated Dec. 23, 2010 (7 pages).
"International Preliminary Report on Patentability," for PCT/US2009/059424 dated May 5, 2011 (7 pages).
"International Preliminary Report on Patentability," for PCT/US2014/015932, dated Aug. 18, 2015 (9 pages).
"International Search Report & Written Opinion," for PCT/US2007/078417, dated Jan. 22, 2009 (14 pages).
"International Search Report & Written Opinion," for PCT/US2014/015932, dated May 22, 2014 (11 pages).
"International Search Report & Written Opinion," for PCT/US2014/062902, dated Feb. 18, 2015 (12 pages).
"International Search Report and Written Opinion," for PCT Application No. PCT/US2016/022110, dated May 24, 2016 (12 pages).
"International Search Report," for PCT/US2009/046750 dated Jul. 20, 2010 (4 pages).
"International Search Report," for PCT/US2009059424 dated Apr. 21, 2011 (4 pages).
Joshi, S. et al., "High Shear Deformation to Produce High Strenght and Energy Absorption in MG Alloys," Editor Martyn Alderman et al., Magnesium Technology 2014, TMS (The Minerals, Metals, and Materials Society), 2014, Wiley Publishers, pp. 83-88.
Khan, Mohammad N. "Solidification study of commercial magnesium alloys," Master's Thesis, Concordia University, Montreal, Quebec, Canada, Oct. 2009 (105 pages).
Kim, et al., "Continuous Casting of Magnesium Alloy Billet Using Electromagnetic Techniques," Materials Science Forum vols. 654-656, Nie and Morton, Jun. 2010 (3 pages) 787-790.
Milner, F. et al., "Microstructural Evolution and Its Relationship to the Mechanical Properties of MG AZ31B Friction Stir Back Extruded Tubes," Editor Martyn Alderman et al., Magnesium Technology 2014, TMS (The Minerals, Metals, and Materials Society), 2014, Wiley Publishers, pp. 263-268.
"Non-Final Office Action," for U.S. Appl. No. 13/284,467 dated Aug. 6, 2015 (11 pages).
"Office Action," for U.S. Appl. No. 14/178,869 dated Oct. 19, 2015 (9 pages).
Park, Won-Wook et al., "Microstructural change and precipitation hardening in melt-spun Mg-X-Ca alloys," Science and Technology of Advanced Materials (2001), 2:1 73-78 (6 pages).
"Response to Communication Pursuant to Article 94(3) EPC," for European Patent Application No. 15176192.1, filed with the EPO Mar. 21, 2016 (58 pages).
"Response to Communication Pursuant to R161(1) and 162 EPC," for European Patent Application No. 14706247.5, dated Oct. 30, 2015 and filed with the EPO Dec. 17, 2015 (17 pages.
"Response to Non-Final Office Action," for U.S. Appl. No. 13/284,467, dated Aug. 6, 2015 and filed with the USPTO Jan. 6, 2016 (6 pages).
"Response to Non-Final Office Action," for U.S. Appl. No. 14/178,869, dated Oct. 19, 2015 and filed with the USPTO Mar. 15, 2016 (9 pages).
Zhou, Y. et al., "Microstructure Evolution and Mechanical Behavior of MG-10Gd-3Y-0.4Zr Alloy Processed by ECAP at High Temperature," Editor Martyn Alderman et al., Magnesium Technology 2014, TMS (The Minerals, Metals, and Materials Society), 2014, Wiley Publishers, pp. 511-516 (6 pages).
Final Office Action for U.S. Appl. No. 15/392,547 dated Aug. 16, 2018 (19 pages).
First Office Action for Chinese Patent Application No. 201480071292.6 dated Jun. 6, 2018 (9 pages).
Office Action for Japanese Patent Application No. 2016-526876 dated Jul. 3, 2018 (13 pages) with English translation.
Communication Pursuant to Article 94(3) EPC for European Patent Application No. 16711107.9 dated Dec. 21, 2018 (7 pages).
Non-Final Office Action for U.S. Appl. No. 15/352,111 dated Jan. 31, 2019 (30 pages).
Office Action for Japanese Patent Application No. 2016-526876 dated Jan. 29, 2019 (7 pages) with English Translation.
Response to Final Rejection dated Aug. 16, 2018, for U.S. Appl. No. 15/392,547, submitted via EFS-Web on Jan. 15, 2019, 12 pages.
Non Final Office Action for U.S. Appl. No. 15/358,636 dated Apr. 11, 2019 (36 pages).

(56) References Cited

OTHER PUBLICATIONS

Response to Non-Final Rejection dated Jan. 31, 2019, for U.S. Appl. No. 15/352,111, submitted via EFS-Web on Apr. 18, 2019, 7 pages.
Second Office Action for Chinese Patent Application No. 201480071292.6 dated Feb. 19, 2019 (12 pages) with English Translation.
Non Final Office Action for U.S. Appl. No. 15/392,547 dated Mar. 22, 2019 (20 pages).
Final Office Action for U.S. Appl. No. 15/358,636 dated Oct. 17, 2019 (17 pages).
Final Office Action for U.S. Appl. No. 15/352,111 dated May 2, 2019 (15 pages).
Friedrich, Horst E. et al., "Magnesium Technology—Metallurgy, Design Data, Applications," Springer, 2006 (22 pages).
Hermawan, Hendra "Biodegradable Metals—From Concept to Applications," Springer, 2012 (8 pages).
Jin, Li et al., "Mechanical properties and microstructure of AZ31 Mg Alloy processed by two-step equal channel angular extrusion," Materials Letters, vol. 59, 2005 (4 pages).
Lee, Y. C. et al., "The Role of Solute in Grain Refinement of Magnesium," Metallurgical and Materials Transactions A, vol. 31A, Nov. 2000 (12 pages).
Notice of Opposition for European Patent Application No. 14706247.5 on behalf of BIOTRONIK AG, dated May 14, 2019 (23 pages).
Rad, Hamid R. et al., "Characterization and corrosion behavior of biodegradable Mg—Ca and Mg—Ca—Zn implant alloys," Applied Mechanics and materials, vol. 121, Oct. 24, 2011 (6 pages).
Serruys, Patrick W. et al., "Handbook of Coronary Stents," Martin Dunitz Ltd., 2000 (11 pages).
Wu, Qiong et al., "The microstructure and properties of cyclic extrusion compression treated Mg—Zn—Y—Nd Alloy for vascular stent application," Journal of the Mechanical Behavior of Biomedical Materials, vol. 8, Apr. 2012 (8 pages).
Notice of Allowance for U.S. Appl. No. 15/352,111 dated Aug. 30, 2019 (12 pages).
Response to Final Rejection dated May 2, 2019 for U.S. Appl. No. 15/352,111, submitted via EFS-Web on Aug. 21, 2019, 5 pages.
Response to Non-Final Rejection dated Apr. 11, 2019 for U.S. Appl. No. 15/358,636, submitted via EFS-Web on Aug. 21, 2019, 9 pages.

\* cited by examiner

BIOERODIBLE MAGNESIUM ALLOY MICROSTRUCTURES FOR ENDOPROSTHESES

REFERENCE TO RELATED APPLICATIONS

This application claims priority under 35 U.S.C. § 119(e) to U.S. Provisional Application No. 62/131,554, filed Mar. 11, 2015, the entire disclosure of which is herein incorporated by reference.

TECHNICAL FIELD

This disclosure relates to microstructures for bioerodible magnesium alloys used in endoprostheses and methods of producing those microstructures.

BACKGROUND

Endoprostheses can be used to replace a missing biological structure, support a damaged biological structure, and/or enhance an existing biological structure. Frequently, only a temporary presence of the endoprosthesis in the body is necessary to fulfill the medical purpose. Surgical intervention to remove endoprostheses, however, can cause complications and may not even be possible. One approach for avoiding a permanent presence of all or part of an endoprosthesis is to form all or part of the endoprosthesis out of bioerodible material. The term "bioerodible" as used herein is understood as the sum of microbial procedures or processes solely caused by the presence of endoprosthesis within a body, which results in a gradual erosion of the structure formed of the bioerodible material.

At a specific time, the endoprosthesis, or at least the part of the endoprosthesis that includes the bioerodible material, loses its mechanical integrity. The erosion products are mainly absorbed by the body, although small residues can remain under certain conditions. A variety of different bioerodible polymers (both natural and synthetic) and bioerodible metals (particularly magnesium and iron) have been developed and are under consideration as candidate materials for particular types of endoprostheses. Although magnesium and magnesium alloys have been explored as candidate materials for bioerodible endoprostheses in the past, the mechanical and erosion properties of magnesium and magnesium alloys have presented certain difficulties that make the use of a bioerodible magnesium metal or alloy in certain endoprostheses, such as stents, impractical.

SUMMARY

In Example 1, a bioerodible endoprosthesis provided herein includes a bioerodible body including an alloy that includes at least 85 weight percent magnesium and at least one high-melting-temperature element having a melting temperature of greater than 700° C. The alloy has a microstructure including equiaxed magnesium-rich phase grains and high-melting-temperature intermetallic phases. The equiaxed magnesium-rich phase grains have an average grain diameter of less than or equal to 10 microns (or about 0.0004 inches). The high-melting-temperature intermetallic phases can include at least 30 weight percent of one or more high-melting-temperature elements and have an average longest dimension of 3 microns or less (or 0.0001 inches or less).

In Example 2, the endoprosthesis of Example 1, wherein the at least one high-melting-temperature element is a rare earth metal.

In Example 3, the endoprosthesis of Example 1 or Example 2, wherein the at least one high-melting-temperature element has a melting temperature of at least 1,000° C.

In Example 4, the endoprosthesis of one of Examples 1-3, wherein the at least one high-melting-temperature element is selected from the group consisting of neodymium, tin, yttrium, cerium, lanthanum, and gadolinium.

In Example 5, the endoprosthesis of one of Examples 1-4, wherein the alloy includes between 0.5 and 5.0 weight percent of the at least one high-melting-temperature element.

In Example 6, the endoprosthesis of one of Examples 1-5, wherein the alloy further includes aluminum, zinc, or a combination thereof.

In Example 7, the endoprosthesis of Example 6, wherein the microstructure further includes low-melting-temperature intermetallic phases having an average longest dimension of 1 micron or less (or 0.00004 inches or less), the low-melting-temperature intermetallic phases including aluminum, zinc, or a combination thereof.

In Example 8, the endoprosthesis of Example 6 or Example 7, wherein the low-melting-temperature intermetallic phases including Mg17Al12.

In Example 9, the endoprosthesis of one of Examples 1-8, wherein the alloy has an elastic modulus of between 39 GPa and 44 GPa, a 0.2% offset yield strength of between 150 MPa and 350 MPa, an ultimate tensile strength of between 250 MPa and 400 MPa, and a tensile reduction in area of at least 30%.

In Example 10, the endoprosthesis of one of Examples 1-9, wherein the bioerodible body includes between 5 and 11 weight percent aluminum, between 0.1 and 3.0 weight percent zinc, up to 0.3 weight percent manganese, and between 0.6 and 1.5 weight percent neodymium, and balance magnesium.

In Example 11, the endoprosthesis of one of Examples 1-10, wherein the endoprosthesis is a stent including a plurality of struts, wherein the struts have a width to thickness ratio of less than 1.2.

In Example 12, a method of forming an endoprosthesis defined by one of Examples 1-11 that includes cooling a solution including at least 85 weight percent magnesium and at least one high-melting-temperature element from a temperature of equal to or greater than the melting temperature of the at least one high-melting-temperature element to a temperature of 650° C. or less at a rate of at least 3.0° C. per second to form a cast alloy. The method can also include performing at least one high-strain process on the cast alloy to form the microstructure of one of Examples 1-11.

In Example 13, the method of Example 12, wherein the solution is cooled from a temperature of equal to or greater than the at least one high-melting-temperature element to a temperature of 650° C. or less at a rate of at least 30° C. per second.

In Example 14, the method of Example 12 or Example 13, wherein the at least one high-strain process is an equal-channel, high-strain process performed at a temperature of less than 400° C.

In Example 15, the method of Example 14, wherein the cooling of the solution forms a supersaturated flake, further including consolidating the supersaturated flake into a billet, wherein the billet is processed through at least two equal-channel, high-strain processes at different temperatures, wherein a first equal-channel, high-strain process occurs at a first time and is performed at a higher temperature than a second equal-channel, high-strain process that occurs at a second time occurring after the first time, wherein the first equal-channel, high-strain process is performed at a temperature of between 250° C. and 400° C. and the second equal-channel, high-strain process is performed at a temperature of between 150° C. and 300° C.

In Example 16, a bioerodible endoprosthesis includes a bioerodible body including an alloy that includes at least 85 weight percent magnesium and at least one high-melting-temperature element having a melting temperature of greater than 700° C. The alloy has a microstructure including equiaxed magnesium-rich phase grains and optionally high-melting-temperature intermetallic phases. The equiaxed magnesium-rich phase grains have an average grain diameter of less than or equal to 10 microns (or about 0.0004 inches) and the high-melting-temperature intermetallic phases, if present, include at least 20 weight percent of one or more high-melting-temperature elements and have an average longest dimension of 3 microns or less (or 0.0001 inches or less).

In Example 17, the endoprosthesis of Example 16, wherein the at least one high-melting-temperature element is a rare earth metal.

In Example 18, the endoprosthesis of Example 16, wherein the at least one high-melting-temperature element has a melting temperature of at least 1,000° C.

In Example 19, the endoprosthesis of Example 16, wherein the at least one high-melting-temperature element is selected from the group consisting of neodymium, tin, yttrium, cerium, lanthanum, and gadolinium.

In Example 20, the endoprosthesis of Example 16, wherein the alloy includes between 0.5 and 5.0 weight percent of the at least one high-melting-temperature element.

In Example 21, the endoprosthesis of Example 16, wherein the high-melting-temperature intermetallic phases are primarily centered upon grain boundaries between equiaxed magnesium-rich phase grains and do not extend into the equiaxed magnesium-rich phase grain interior by more than 0.3 microns (or 0.0001 inches) from a grain boundary when viewed at 200-500× magnification on a metallography plane.

In Example 22, the endoprosthesis of Example 16, wherein the alloy further includes aluminum, zinc, manganese, or a combination thereof.

In Example 23, the endoprosthesis of Example 22, wherein the microstructure further includes low-melting-temperature intermetallic phases having an average longest dimension of 1 micron or less (or 0.00004 inches or less), the low-melting-temperature intermetallic phases including aluminum, zinc, manganese, or a combination thereof.

In Example 24, the endoprosthesis of Example 23, wherein the low-melting-temperature intermetallic phases include Mg17Al12.

In Example 25, the endoprosthesis of Example 16, wherein the alloy has an elastic modulus of between 39 GPa and 44 GPa, a 0.2% offset yield strength of between 150 MPa and 350 MPa, an ultimate tensile strength of between 250 MPa and 400 MPa, and a tensile reduction in area of at least 30%.

In Example 26, the endoprosthesis of Example 16, wherein the alloy maintains its initial elastic modulus, yield strength, ultimate tensile strength, and a tensile RIA within ±10% following storage for 180 days at a temperature of between 20° C. and 25° C. and a relative humidity of less than 30%.

In Example 27, the endoprosthesis of Example 16, wherein the bioerodible body includes between 5 and 11 weight percent aluminum, between 0.1 and 3.0 weight percent zinc, up to 0.3 weight percent manganese, and between 0.6 and 1.5 weight percent neodymium, and balance magnesium.

In Example 28, the endoprosthesis of Example 16, wherein the endoprosthesis is a stent including a plurality of struts, wherein the struts have a width to thickness ratio of less than 1.2.

In Example 29, a method of forming an endoprosthesis includes cooling a solution including at least 85 weight percent magnesium and at least one high-melting-temperature element from a temperature of equal to or greater than the melting temperature of the at least one high-melting-temperature element to a temperature of 650° C. or less at a rate of at least 3.0° C. per second to form a cast alloy. The method can also include performing at least one high-strain process on the cast alloy to form a microstructure of equiaxed magnesium-rich phase grains and high-melting-temperature intermetallic phases, the equiaxed magnesium-rich phase grains having an average grain diameter of less than or equal to 10 microns (or about 0.0004 inches) and the high-melting-temperature intermetallic phases having an average longest dimension of 3 microns or less (or 0.0001 inches or less).

In Example 30, the method of Example 29, wherein the solution is cooled from a temperature of equal to or greater than the at least one rare earth metal to a temperature of 650° C. or less at a rate of at least 30° C. per second.

In Example 31, the method of Example 29, wherein the at least one high-strain process is an equal-channel, high-strain process performed at a temperature of less than 400° C.

In Example 32, the method of Example 31, wherein the cooling of the solution forms a supersaturated flake, further including consolidating the supersaturated flake into a billet, wherein the billet is processed through at least two equal-channel, high-strain processes at different temperatures, wherein a first equal-channel, high-strain process occurs at a first time and is performed at a higher temperature than a second equal-channel, high-strain process that occurs at a second time occurring after the first time, wherein the first equal-channel, high-strain process is performed at a temperature of between 250° C. and 400° C. and the second equal-channel, high-strain process is performed at a temperature of between 150° C. and 300° C.

In Example 33, the method of Example 29, wherein the solution further includes aluminum, zinc, manganese, or a combination thereof.

In Example 34, the method of Example 33, wherein the microstructure further includes low-melting-temperature intermetallic phases having an average longest dimension of 1 micron or less (or 0.00004 inches or less), the low-melting-temperature intermetallic phases including aluminum, zinc, manganese, or a combination thereof.

In Example 35, the method of Example 29, wherein the solution includes between 5 and 11 weight percent aluminum, between 0.1 and 3.0 weight percent zinc, up to 0.3 weight percent manganese, and between 0.6 and 1.5 weight percent neodymium, and balance magnesium.

In some aspects, a bioerodible endoprosthesis can include a bioerodible body including an alloy including at least 85 weight percent magnesium and at least one high-melting-temperature element having a melting temperature of greater than 700° C. The alloy can have a microstructure including equiaxed magnesium-rich phase grains and high-melting-temperature intermetallic phases. The equiaxed magnesium-rich phase grains have an average grain diameter of less than or equal to 10 microns (or about 0.0004 inches) and the high-melting-temperature intermetallic phases have an average longest dimension of 3 microns or less (or 0.0001 inches or less). In some cases, the high-melting-temperature intermetallic phases can include at least 10 weight percent of one or more high-melting temperature elements. In some cases, the high-melting-temperature intermetallic phases can include at least 20 weight percent of one or more high-melting temperature elements. In some cases, the high-melting-temperature intermetallic phases can include at least 30 weight percent of one or more high-melting temperature elements. In some cases, the at least one high-melting-temperature element can be a rare earth metal. In some cases, the at least one high-melting-temperature element has a melting temperature of at least 1,000° C. In some cases, the at least one high-melting-temperature element is selected from the group consisting of neodymium, tin, yttrium, cerium, lanthanum, and gadolinium. In some cases, the high-melting-temperature element can be manganese. In some cases, the alloy includes between 0.5 and 5.0 weight percent of the at least one high-melting-temperature element. In some cases, the high-melting-temperature intermetallic phases are primarily centered upon grain boundaries between equiaxed magnesium-rich phase grains and do not extend into the equiaxed magnesium-rich phase grain interior by more than 0.3 microns (or 0.0001 inches) from the grain boundary when viewed at 200-500× magnification on a metallography plane.

In some cases, the alloy can further include one or more low-melting-temperature elements. In some cases, the alloy can further include aluminum, zinc, or a combination thereof. In some cases, the microstructure further includes low-melting-temperature intermetallic phases having an average longest dimension of 1 micron or less (or 0.00004 inches or less). In some cases, the low-melting-temperature intermetallic phases include aluminum, zinc, or a combination thereof. In some cases, the low-melting-temperature intermetallic phases can include Mg17Al12.

In some cases, the alloy can have an elastic modulus of between 39 GPa and 44 GPa, a 0.2% offset yield strength of between 150 MPa and 350 MPa, an ultimate tensile strength of between 250 MPa and 400 MPa, and/or a tensile reduction in area of at least 30%.

In some cases, the bioerodible body includes between 5 and 11 weight percent aluminum, between 0.1 and 3.0 weight percent zinc, up to 0.3 weight percent manganese, and between 0.6 and 1.5 weight percent neodymium, and balance magnesium.

In some cases, the endoprosthesis can be a stent including a plurality of struts, wherein the struts have a width to thickness ratio of less than 1.2.

In some aspects, method of forming an endoprosthesis provided herein can include cooling a solution including at least 85 weight percent magnesium and at least one high-melting-temperature element from a temperature of equal to or greater than the melting temperature of the at least one high-melting-temperature element to a temperature of 650° C. or less at a rate of at least 3.0° C. per second to form a cast alloy. In some cases, the cast alloy can include a supersaturation of the at least one high-melting-temperature element within a magnesium phase. In some cases, methods provided herein can include performing at least one high-strain process on the cast alloy to form a microstructure provided herein. In some cases, the solution is cooled from a temperature of equal to or greater than the at least one high-melting-temperature element to a temperature of 650° C. or less at a rate of at least 30° C. per second. In some cases, the at least one high-strain process is an equal-channel, high-strain process performed at a temperature of less than 400° C. In some cases, the cooling of the solution forms a supersaturated flake. In some cases, the method can include consolidating the supersaturated flake into a billet. The billet can then be processed through at least two equal-channel, high-strain processes at different temperatures. A first equal-channel, high-strain process can occur at a first time at a higher temperature than a second equal-channel, high-strain process occurring at a second time after the first time. In some cases, the first equal-channel, high-strain process can be performed at a temperature of between 250° C. and 400° C. and the second equal-channel, high-strain process can be performed at a temperature of between 150° C. and 300° C.

Microstructures provided herein can have more consistent corrosion properties and improved mechanical properties than microstructures containing permanent intermetallic phase particles that form during solidification of the ingot at temperatures greater than the solidification temperature for magnesium-aluminum or magnesium-zinc or ternary compositions of Mg—Al—Zn. An endoprosthesis including a bioerodible body having a microstructure provided herein is that the resulting endoprosthesis' mechanical properties and degradation rate can be tailored to maintain desired mechanical properties over a desired period of time and an optimal bioerosion rate. A bioerodible body having a microstructure provided herein can have improved ductility as compared to similar alloys having different microstructures.

The details of one or more embodiments are set forth in the accompanying drawings and the description below. Other features, objects, and advantages will be apparent from the description and drawings, and from the claims.

DESCRIPTION OF DRAWINGS

FIG. 3A depicts an example of a vascular valve. FIG. 3B depicts an example of a heart valve. FIG. 3C depicts an example of an artificial heart. FIG. 3D depicts an example of a bone and joint implant. FIG. 3E depicts an example of a vascular filter.

DETAILED DESCRIPTION

Endoprostheses provided herein can include magnesium-based multi-phased alloys having microstructures provided herein, which demonstrate consistent corrosion rates and mechanical properties, including improved ductility.

Figure 1:
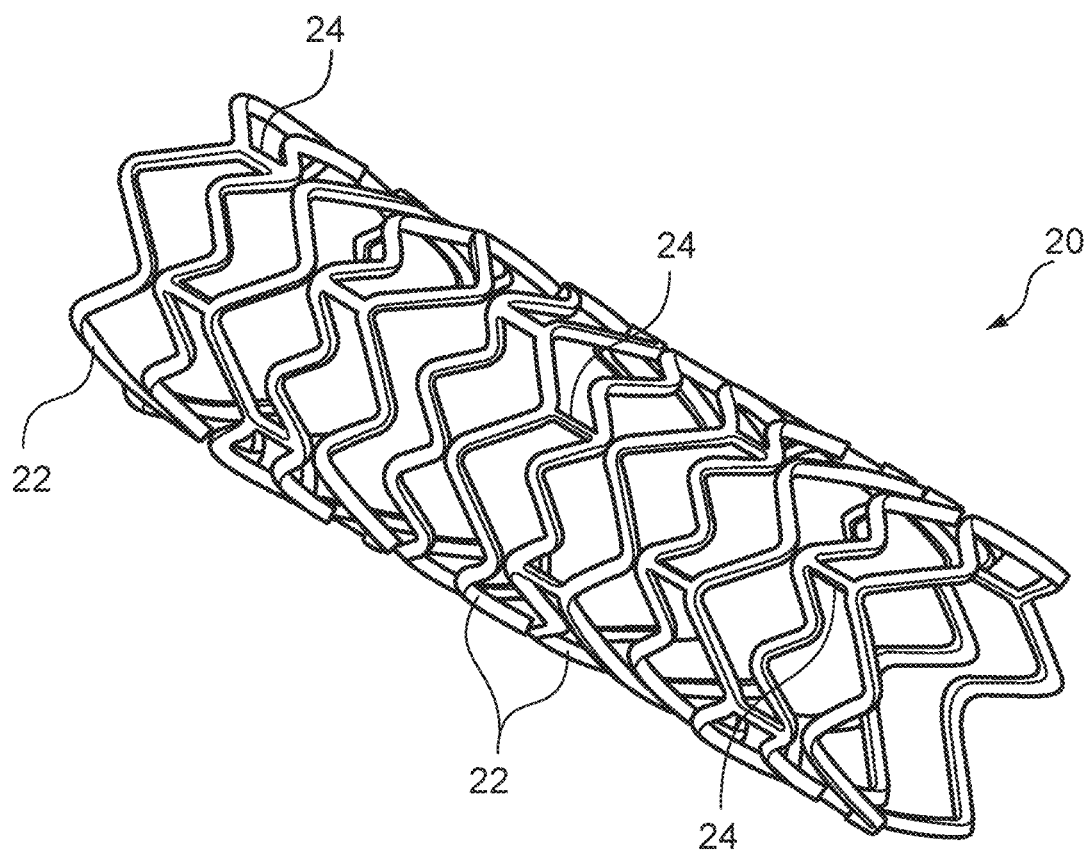
FIG. 1 is a perspective view of a representative stent which can include a bioerodible body having a microstructure provided herein.

In some cases, a stent 20, such as shown in FIG. 1, can include a magnesium-based multi-phased alloy having a microstructure provided herein. Stent 20 includes a pattern of interconnected struts forming a structure that contacts a body lumen wall to maintain the patency of the body lumen. In some cases, stent 20 can have the form of a tubular member defined by a plurality of bands 22 and a plurality of connectors 24 that extend between and connect adjacent bands. During use, bands 22 can be expanded from an initial, small diameter to a larger diameter to anchor the stent 20 against a wall of a vessel, thereby maintaining the patency of the vessel. Connectors 24 can provide stent 20 with flexibility and conformability that allows the stent to adapt to the contours of the vessel.

Figure 3A:
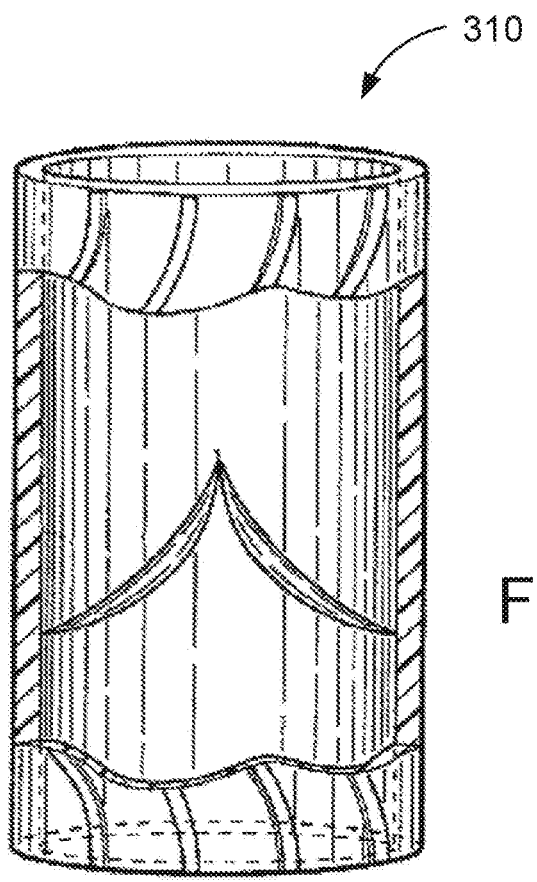
FIGS. 3A-3E depict additional examples of endoprostheses that can include a bioerodible body having a microstructure provided herein.
Figure 3B:
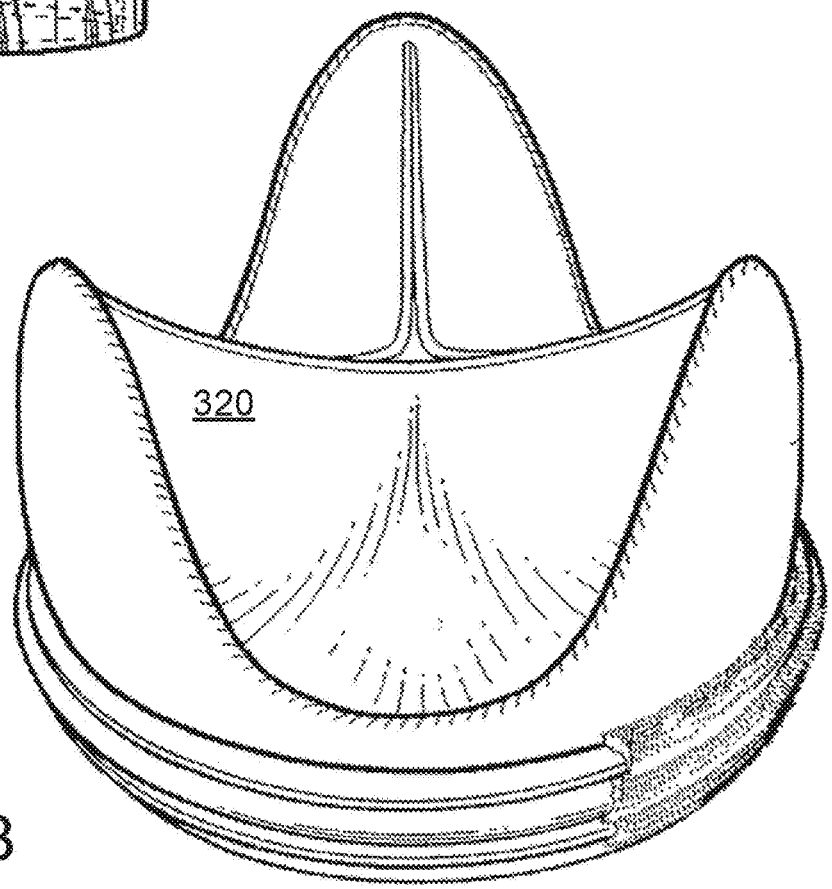
Figure 3C:
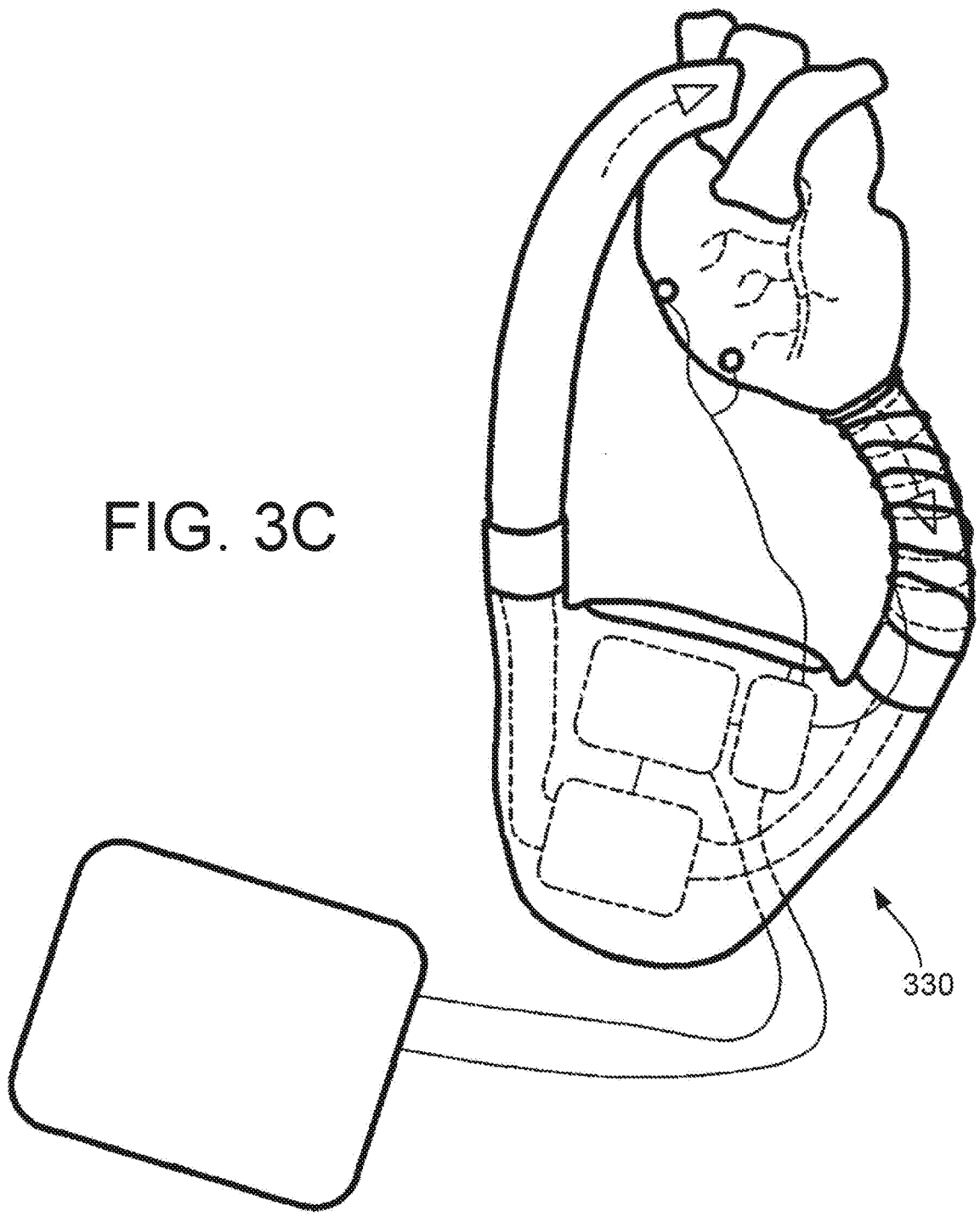
Figure 3D:
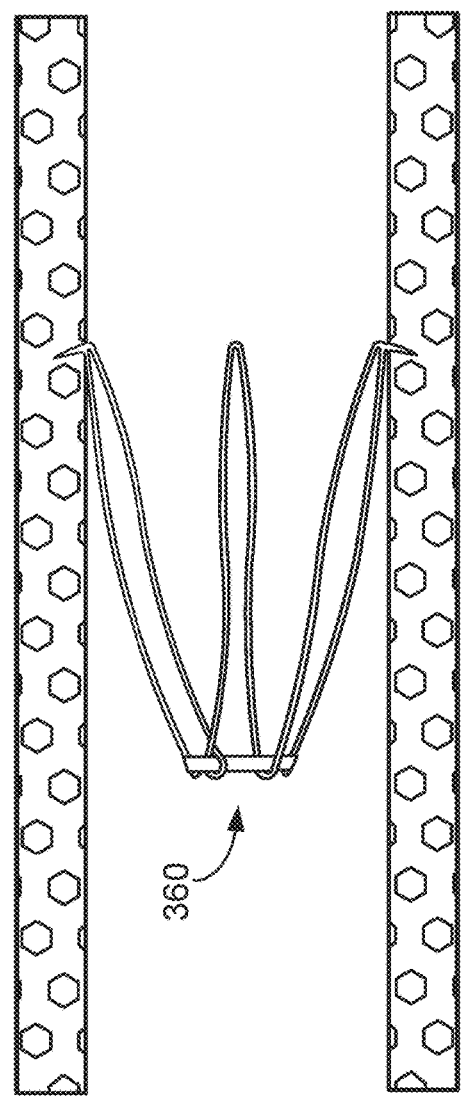
Figure 3E:
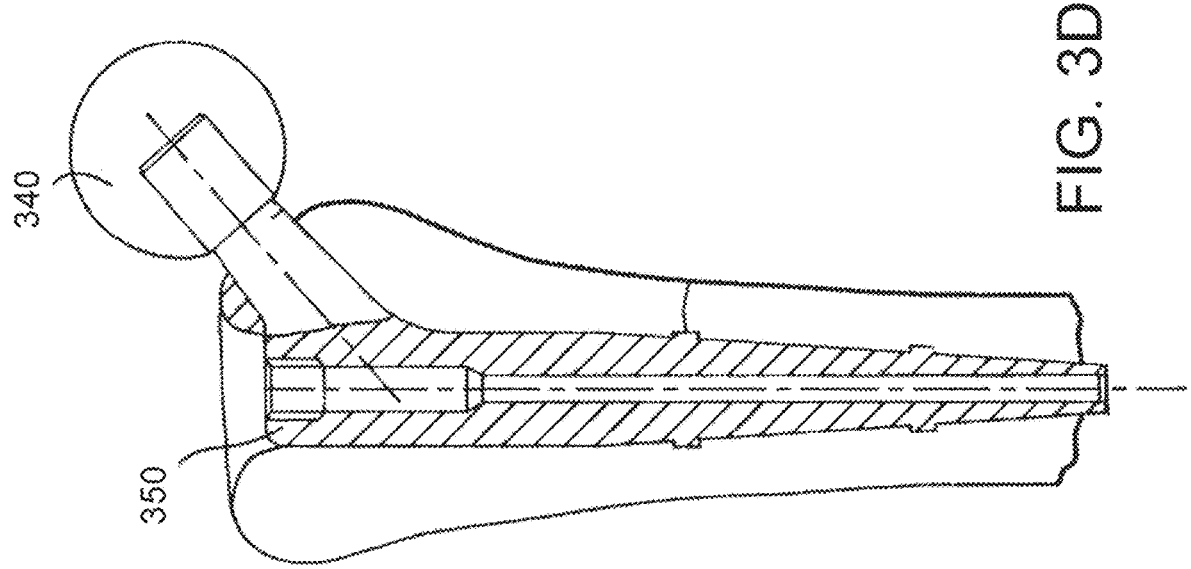

In some cases, a stent 20 can include at least one strut adapted to erode under physiological conditions. In some cases, stent 20 is fully bioerodible. Examples of other suitable implantable medical devices that can include at least one bioerodible body include vascular valves such as a vascular valve 310 depicted in FIG. 3A; heart valves such as a heart valve 320 depicted in FIG. 3B; artificial hearts such as an artificial heart 330 depicted in FIG. 3C; joint and bone implants such as a joint implant 340 and a bone implant 350 depicted in FIG. 3D; vascular filters such as a vascular filter 360 depicted in FIG. 3E; and non-vascular stents for treatment of benign and malignant cancerous occlusions in the digestive tract, airways, and ducts within the eyes.

Endoprostheses provided herein have a bioerodible body that includes magnesium alloyed with at least one high-melting-temperature element. As used herein, a "high-melting-temperature element" is an element that has a melting temperature of at least 700° C. when pure. In some cases, endoprostheses provided herein can include magnesium alloyed with a high-melting-temperature element having a melting temperature of at least 800° C. when pure, of at least 900° C. when pure, of at least 1,000° C. when pure, of at least 1,100° C. when pure, or of at least 1,200° C. when pure. In some cases, endoprostheses provided herein can include magnesium alloyed with a high-melting-temperature element that is a rare earth metal. In some cases, a high-melting-temperature element can be neodymium, tin, yttrium, cerium, lanthanum, and/or gadolinium.

Figure 7:
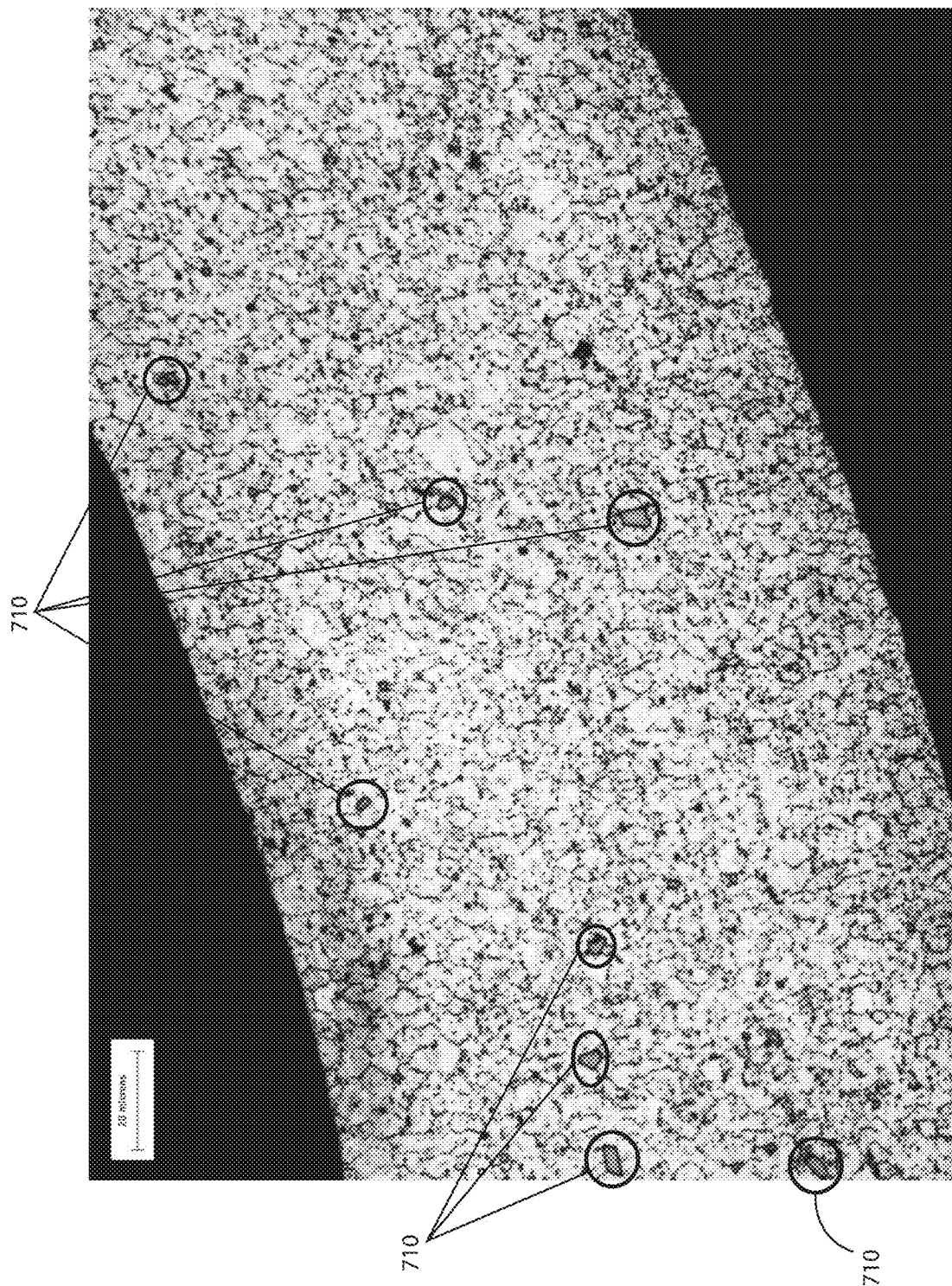
FIG. 7 is a cross-sectional view of a stent strut having high-melting-temperature intermetallic phases.

Endoprostheses provided herein can include a microstructure that includes equiaxed magnesium-rich phase grains having an average grain diameter of less than or equal to 10 microns (or about 0.0004 inches) and high-melting-temperature intermetallic phases having an average longest dimension of 3 microns or less (or 0.0001 inches or less). As used herein, a "high-melting-temperature intermetallic phase" is an intermetallic phase that has a melting temperature of at least 700° C. In some cases, endoprostheses provided herein can include a high-melting-temperature intermetallic phase that melts at a temperature of at least 800° C., of at least 900° C., of at least 1,000° C., of at least 1,100° C., or of at least 1,200° C. The high-melting-temperature intermetallic phases can include at least 30 weight percent of one or more high-melting-temperature elements. Methods of forming an endoprosthesis provided herein can use rapid-solidification techniques to minimize and/or limit the formation of high-melting-temperature intermetallic phases. High-melting-temperature intermetallic phases resist manipulation by solid-state processing techniques, such as thermal exposure. Other low-melting-temperature intermetallic phases, such as beta phase precipitates including aluminum, can break up and/or re-precipitated into fine structures primarily along grain boundaries when manipulated using solid-state processing techniques, such as those disclosed in U.S. Patent Application Publication No. 2014/0236284, which is hereby incorporated by reference. As used herein, a "low-melting-temperature intermetallic phase" is an intermetallic phase that has a melting temperature of less than 650° C. High-melting-temperature intermetallic phases, however, can remain present even after undergoing solid state thermal exposure and high plastic deformation processing. When these High-melting-temperature intermetallic phases intersect the surface of the stent, they serve as initiation sites for corrosive pitting. Instead of providing uniform surface erosion and a uniform stent degradation rate, High-melting-temperature intermetallic phases can cause localized corrosion and cause early strut fracture to occur. For example, FIG. 7 depicts an exemplary cross-section of an AZNd magnesium alloy stent tubing made by casting an alloy ingot using conventional casting techniques; heat treating the ingot to homogenize the ingot; sizing the ingot by pre-extrusion forging; rolling and/or machining for Equal-Channel Angular Extrusion ("ECAE") and/or Equal-Channel Angular Pressing ("ECAP"); passing the ingot through the ECAE or ECAP machinery to refine the microstructure; extruding the rod to form a stent tube; and laser machining and/or electropolishing the tube to form the stent structure. Although low-melting-temperature intermetallic phases shown in FIG. 7 have re-precipitated or migrated to be aligned primarily along grain boundaries, large high-melting-temperature intermetallic phases 710, as shown in the circled region, can remain in the microstructure. Methods of making an endoprosthesis provided herein can minimize the size and number of high-melting-temperature intermetallic phases in magnesium alloys used in endoprostheses provided herein.

In some cases, bioerodible bodies found in endoprostheses provided herein can include a microstructure including equiaxed or elongated magnesium-rich first-phase grains and a plurality of high-melting-temperature intermetallic phases having a longest average dimension of 3 microns or less (or 0.0001 inches or less). In some cases, bioerodible bodies found in endoprostheses provided herein can include high-melting-temperature intermetallic phases each having a longest dimension of 5 microns or less (or 0.0002 inches or less). In some cases, bioerodible bodies found in endoprostheses provided herein can include high-melting-temperature intermetallic phases having an average longest dimension of 2.5 microns or less (or 0.00001 inches or less), 2.0 microns or less (or 0.00008 inches or less), 1.5 microns or less (or 0.00006 inches or less), 1.0 microns or less (or 0.00004 inches or less), or 0.5 microns or less (or 0.00002 inches or less). In some cases, bioerodible bodies found in endoprostheses provided herein can include high-melting-temperature intermetallic phases each having a longest dimension of 4.0 microns or less (or 0.00016 inches or less), 3.0 microns or less (or 0.0001 inches or less), 2.0 microns or less (or 0.00008 inches or less), 1.5 microns or less (or 0.00006 inches or less), 1.0 microns or less (or 0.00004 inches or less), or 0.5 microns or less (or 0.00002 inches or less). In some cases, the size and number of high-melting-temperature intermetallic phases can be determined by the alloy composition, particularly the percentage of high-melting-temperature elements found in the alloy, and in a solution of the alloy constituents from a temperature above the melting temperature of the high-melting-temperature elements to a temperature of about 650° C. or less.

In some cases, bioerodible bodies found in endoprostheses provided herein can include continuous or discontinuous low-melting-temperature intermetallic phases in grain boundaries between the equiaxed or elongated magnesium-rich first-phase grains. In some cases, the low-melting-temperature intermetallic phases can be continuous. In some cases, the low-melting-temperature intermetallic phases can be discontinuous.

The first-phase grains can include at least 50 weight percent magnesium and the high-melting-temperature intermetallic phases can include at least 30 weight percent of one or more high-melting-temperature elements. In some cases, first-phase grains provided herein can include at least 60 weight percent magnesium, at least 70 weight percent magnesium, at least 80 weight percent magnesium, or at least 90 weight percent magnesium in the solid solution. In some cases, first-phase grains provided herein include between 50 weight percent and 98 weight percent magnesium, between 60 weight percent and 96 weight percent magnesium, between 70 weight percent and 94 weight percent magnesium, between 80 weight percent and 93 weight percent magnesium, or between 90 weight percent and 92 weight percent magnesium in a solid solution.

First-phase grains provided herein include a sub-saturation, saturation, or super saturation of at least one high-melting-temperature element with a melting temperature greater than 700° C., such as manganese or a rare earth metal such as neodymium. In some cases, the microstructure constituents may be a solid solution phase containing magnesium, high-melting-temperature elements, and low-melting-temperature elements. As used herein, a "low-melting-temperature element" is an element with a melting temperature of less than 650° C. when pure. When the alloy is cast from an entirely liquid form to a temperature of less than 650° C., the melting temperature of high-melting-temperature phases of magnesium can precipitate during solidification of the ingot. In some cases, the longest dimension of high-melting-temperature phase precipitates can be limited to less than 3 microns (or 0.0001 inches), to less than 1.0 micron (or 0.00004 inches), or to less than 0.5 microns (or 0.00002 inches). In some cases, the total area of a cross-section of the ingot made up of high-melting-temperature intermetallic phases can be no more than 10% when examining a fully manufactured component that has been machined into the form of an unetched cross-sectioned metallography sample at magnifications between 100 and 500×. There may also be low-melting-temperature intermetallic compounds and/or beta phase particles in the microstructure.

Intermetallic phases or compounds are considered to be a phase with a relatively narrow range of composition in comparison to other phases. For example, an alpha Mg—Al phase has a wide range of composition whereas $Al_4Nd$ has a narrow range of composition. In some cases, first-phase grains provided herein include at least 0.5 weight percent of one or more high-melting-temperature elements, at least 0.6 weight percent of one or more high-melting-temperature elements, at least 0.7 weight percent of one or more high-melting-temperature elements, at least 0.8 weight percent of one or more high-melting-temperature elements, at least 1.0 weight percent of one or more high-melting-temperature elements, at least 1.25 weight percent of one or more high-melting-temperature elements, at least 1.5 weight percent of one or more high-melting-temperature elements, at least 2.0 weight percent of one or more high-melting-temperature elements, at least 2.5 weight percent of one or more high-melting-temperature elements, at least 3.0 weight percent of one or more high-melting-temperature elements, at least 4.0 weight percent of one or high-melting-temperature elements, at least 5.0 weight percent of one or more high-melting-temperature elements, at least 6.0 weight percent of one or more high-melting-temperature elements, at least 7.0 weight percent of one or more high-melting-temperature elements, or at least 8.0 weight percent of one or high-melting-temperature elements. In some cases, first-phase grains provided herein include between 0.5 weight percent and 15.0 weight percent of one or more high-melting-temperature elements, between 0.6 weight percent and 12.0 weight percent of one or more high-melting-temperature elements, between 0.7 weight percent and 10.0 weight percent of one or more high-melting-temperature elements, between 0.8 weight percent and 8.0 weight percent of one or more high-melting-temperature elements, between 1.0 weight percent and 5.0 weight percent of one or more high-melting-temperature elements, between 1.25 weight percent and 3.0 weight percent of one or more high-melting-temperature elements, or between 1.5 weight percent and 2.0 weight percent of one or more high-melting-temperature elements. In some cases, the total amount of high-melting-temperature elements within the bioerodible magnesium alloy is maintained at a level of less than 10.0 weight percent. In some cases, the total amount of high-melting-temperature elements within the bioerodible magnesium alloy is maintained at a level of less than 2.5 weight percent. In some cases, first-phase grains provided herein can include between 0.1 and 3.0 weight percent of a first high-melting-temperature element. In some cases, the first high-melting-temperature elements is yttrium, neodymium, lanthanum, or cerium. For example, in some cases, first-phase grains provided herein can include between 0.6 weight percent and 3.0 weight percent of neodymium, between 0.8 and 1.5 weight percent neodymium, or between 0.09 and 1.2 weight percent of neodymium. In some cases, first-phase grains provided herein can include can also include between 0.1 and 3.0 weight percent of a second high-melting-temperature element. For example, a bioerodible magnesium alloy provided herein can include about 0.5 weight percent yttrium and 0.6 weight percent neodymium. In some cases, the bioerodible magnesium alloy includes three or more high-melting-temperature elements. In some cases, the total amount of high-melting-temperature elements within the bioerodible magnesium alloy is maintained at a level of less than 10.0 weight percent. In some cases, the total amount of high-melting-temperature elements within the bioerodible magnesium alloy is maintained at a level of less than 2.5 weight percent.

In addition to magnesium and at least a first high-melting-temperature element, bioerodible bodies having a microstructure provided herein can additionally include a variety of additional high-melting-temperature elements and/or low-melting-temperature elements, which may be present in the first-phases in the magnesium solid solution, high-melting-temperature intermetallic phases, and/or in low-melting-temperature intermetallic phases. In some cases, a bioerodible body having a microstructure provided herein can include aluminum. In some cases, a bioerodible body having a microstructure provided herein can include zinc. In some cases, a bioerodible body having a microstructure provided herein can include calcium. In some cases, a bioerodible body having a microstructure provided herein can include tin. In some cases, a bioerodible body having a microstructure provided herein can include manganese. In some cases, a bioerodible body having a microstructure provided herein can include high-melting-temperature element such as neodymium. For example, a bioerodible body having a microstructure provided herein can include at least 85 weight percent magnesium, between 5 and 11 weight percent aluminum, between 0.1 and 3 weight percent zinc, and between 0.05 and 0.3 weight percent manganese, between 0.6 and 1.5 weight percent neodymium, up to 100 ppm copper, and up to 175 ppm iron. Other possible bioerodible magnesium alloys include those listed in Tables 1 and 2 below. Examples of other suitable bioerodible magnesium alloys can be found in U.S. Patent Application Publication No. 2012/0059455, which is hereby incorporated by reference in its entirety, particularly the sections describing particular bioerodible magnesium alloys.

TABLE 1

| Alloy Ex. | Zn | Zr | Mn | Y | Nd | Ca | Ag | Fe | Other Elements | Mg |
|---|---|---|---|---|---|---|---|---|---|---|
| WE43 | Not specified | 0.0-1.0 | Not specified | 2.0-6.0 | 1.5-4.5 | Not specified | Not specified | Not specified | 0.5-4.0 of other rare earths metals; 0.0-0.3 Al | Balance |

TABLE 2

| Alloy Example | Al | Zn | Mn | Y | Nd | La | Mg |
|---|---|---|---|---|---|---|---|
| AZNd | 7.3 | 0.6 | 0.1 | — | 0.7 | — | Balance |
| AZY | 7.4 | 0.6 | 0.1 | 0.5 | — | — | Balance |
| AZNdY | 7.0 | 0.6 | 0.2 | 0.5 | 0.6 | — | Balance |
| AZL | 7.0 | 0.5 | 0.2 | — | — | 1.2 | Balance |
| AE82 | 8.0 | 0.5 | 0.2 | 0.5 | 1.0 | — | Balance |

In some cases, the bioerodible body provided herein includes aluminum. In some cases, $Mg_{17}Al_{12}$ low-melting-temperature phases can precipitate in a bioerodible magnesium alloy provided herein during solid state processing and heat treatment. $Mg_{17}Al_{12}$ low-melting-temperature intermetallic phases can be less cathodic than phases that form from other alloy systems such as those containing high-melting-temperature elements, which can provide improved corrosion resistance relative to alloys having more cathodic precipitates (e.g., precipitates containing high-melting-temperature elements can have a greater difference in electromotive voltage difference than the other phases in the microstructure thereby facilitating localized galvanic corrosion and overall localized rapid corrosion rate within the endoprosthesis leading to undesirable early fracture). The low-melting-temperature intermetallic phases can be more noble than the Mg grains and form a corrosion-resistant barrier along grain boundaries and thereby protect the grain interiors as a "grain coating". Aluminum can also form native oxide layers along grain boundaries, which can act as a protective layer for the grains and delay the onset of intergranular corrosion. Smaller grain sizes can also reduce the corrosion rate because corrosion must re-initiate past the protective oxide layer for each grain corroded.

A bioerodible body having a microstructure provided herein can include a variety of different additional high-melting-temperature and low-melting-temperature elements. In some cases, the bioerodible body includes less than 5 weight percent, in sum, of elements other than magnesium, aluminum, zinc, and manganese. In some cases, the bioerodible body includes less than 2 weight percent, in sum, of elements other than magnesium, aluminum, zinc, and manganese. The bioerodible body can consist essentially of magnesium, aluminum, zinc, manganese, and one or more rare earth metals (e.g., neodymium). As used herein, "consisting essentially of" means that the bioerodible body can also include impurities normally associated with the commercially available forms of the constituent elements in amounts corresponding to the amounts found in the commercially available forms of the constituent elements. In some cases, the potential impurity elements of iron, copper, nickel, gold, cadmium, bismuth, sulfur, phosphorous, silicon, calcium, tin, lead and sodium are each maintained at levels of less than 1000 ppm. In some cases, the potential impurity elements of iron, copper, nickel, cobalt, gold, cadmium, bismuth, sulfur, phosphorous, silicon, calcium, tin, lead and sodium are each maintained at levels of less than 200 ppm. Iron, nickel, copper, and cobalt have low solid-solubility limits in magnesium and can serve as active cathodic sites that accelerate the erosion rate of magnesium within a physiological environment. In some cases, each of the impurity elements, e.g., iron, nickel, copper, and cobalt, is maintained at levels of less than 50 ppm. For example, each of the first five alloys listed in Table 2 has no more than 35 ppm of iron.

Equiaxed magnesium-rich first-phase grains. can be considered the alpha phase of the microstructure. Secondary low-melting-temperature phase(s) can include particles present in the grain boundaries between adjacent first-phase grains. In some cases, high-melting temperature elements can be in solution with the magnesium in the first-phase grains. In some cases, small (e.g., less than 0.5 microns or 0.00002 inches in size) high-melting-temperature phases can precipitate either within the first-phase grains or along the interfaces.

In some cases, a secondary low-melting-temperature phase forms a continuous interface between adjacent first-phase grains. In some cases, a continuous interface between adjacent first-phase grains can provide a corrosion resistant barrier between adjacent first-phase grains. In some cases, secondary low-melting-temperature phases are discontinuous in the interface between adjacent first-phase grains. As shown, the first-phase grains have a grain size larger than the size of the particles in the low-melting-temperature secondary phase(s). In some cases, first-phase grains in a microstructure provided herein can have an average grain diameter at least 3 times larger than an average secondary low-melting-temperature phase particle diameter. In some cases, first-phase grains in a microstructure provided herein can have an average grain diameter at least 5 times larger, at least 8 times larger, at least 10 times larger, or at least 20 times larger than an average low-melting-temperature secondary phase particle diameter. In some cases, first-phase grains have an average grain size of 20 microns or less (or 0.0008 inches or less), 15 microns or less (or 0.0006 inches or less), 10 microns or less (or 0.0004 inches or less), 7.5 microns or less (or 0.0003 inches or less), 5 microns or less (or 0.0002 inches or less), or 4 microns or less (or 0.00016 inches or less). In some cases, the first-phase grains have an average grain size of between 0.1 microns (or 0.00004 inches) and 10 microns (or between 0.000004 inches and 0.0004 inches), between 0.5 microns and 5 microns (or between 0.00002 inches and 0.0002 inches), or between 1 micron and 4 microns (or between 0.00004 inches and 0.00016 inches). In some cases, a maximum secondary-low-melting-temperature phase particle (e.g., low-melting-temperature intermetallic or low-melting-temperature secondary phase particle) dimension will be 30 microns or less (0.001 inches or less). In some cases, a secondary-phase particle dimension will be 20 microns or less (or 0.0008 inches or less), 10 microns or less (or 0.0004 inches or less), 5 microns or less (or 0.0002 inches or less), or 1 micron or less (or 0.00004 inches or less). In some cases, at least 90% by volume of the secondary-phase particles can be found along grain boundaries between adjacent first-phase grains. In some cases, the average secondary-phase individual particle diameter or longest dimension is 5 microns or less (or 0.0002 inches or less), 3 microns or less (0.0001 inches or less), 1 micron or less (or 0.00004 inches or less), or 0.5 microns or less (or 0.00002 inches or less). In some cases, the average secondary-phase individual particle diameter or longest dimension is between 0.05 microns and 5 microns (or between 0.000002 inches and 0.0002 inches), between 0.1 microns and 3 microns (or between 0.000004 inches and 0.0001 inches), or between 0.2 microns and 1 micron (or between 0.000008 inches and 0.00004 inches). The microstructure provided herein can have a reduced number of twin bands. In some cases, less than 15% of the alpha grains will have twin bands. In some cases, the number of alpha grains having twin bands can be less than 10%, less than 5%, or less than 1%. In some cases, a stent 20 can be cut and crimped and have a number of alpha grains having twin bands that are less than 10%, less than 5%, or less than 1%.

In some cases, a bioerodible body having a microstructure includes first-phase grains having an average grain size of 20 microns or less (or 0.0008 inches or less) and a secondary low-melting-temperature phase having an average particle diameter of 10 microns or less (or 0.0004 inches or less), 5 microns or less (or 0.0002 inches or less), 1 micron or less (or 0.00004 inches or less) or 0.5 microns or less (or 0.00002 inches or less). In some cases, a microstructure includes first-phase grains having an average grain size of 15 microns or less (or 0.0006 inches or less), 10 microns or less (or 0.0004 inches or less), 7.5 microns or less (or 0.0003 inches or less), and an average secondary low-melting-temperature phase particle diameter of 5 microns or less (or 0.0002 inches or less), 1 micron or less (or 0.00004 inches or less) or 0.5 microns or less (or 0.00002 inches or less). In some cases, a microstructure includes first-phase grains having an average grain size of 5 microns or less (or 0.0002 inches or less) or 4 microns or less (or 0.00016 inches or less) and an average secondary low-melting-temperature phase particle diameter of 1 micron or less (or 0.00004 inches or less) or 0.5 microns or less (or 0.00002 inches or less).

In some cases, a bioerodible body having a microstructure includes first-phase grains having an average grain size of between 1 micron and 5 microns (0.0002 inches) and an average secondary-phase individual particle having a diameter or a longest dimension of between 0.1 microns and 1 micron (or between 0.000004 inches and 0.00004 inches).

In some cases, for example, a bioerodible body can have a microstructure that includes an average grain diameter provided herein and a composition of between 5 and 11 weight percent aluminum, between 0.1 and 3.0 weight percent zinc, up to 0.3 weight percent manganese, and between 0.6 and 1.5 weight percent neodymium, and balance magnesium.

Microstructures and processes provided herein can mitigate a root cause of low material ductility and cracking by producing a body having a reduced volume and size of hard phases or hard particles. The resultant produced body can have a refined Mg solid solution grain size. The microstructures and processes provided herein can be tailored to manifest sufficient ductility in a balloon-expandable stent design such that the Mg alloy stent microstructure would allow the stent to be crimped onto a balloon catheter, wiggled through a long tortuous path, and expanded to fill the diameter of the artery without fracturing. A description of how grain sizes and additional slip planes in a microstructure provided herein can improve the ductility of a bioerodible body (e.g., in a stent or other endoprosthesis) as compared to magnesium alloys having different microstructures can be found in U.S. Patent Application Publication No. 2014/0236284, which is hereby incorporated by reference.

As discussed above, the casting of a magnesium alloy including one or more high-melting-temperature elements in magnesium can result in permanent, high-melting-temperature, intermetallic precipitates in addition to non-permanent, low-melting-temperature, intermetallic phases in an alpha phase. These high-melting-temperature intermetallic phases can form during the solidification of the melted mixture of magnesium and the alloy elements. For example, the casting of a magnesium alloy including at least 85 weight percent magnesium, between 5 and 11 weight percent aluminum, between 0.1 and 3 weight percent zinc, and between 0.05 and 0.3 weight percent manganese, between 0.6 and 1.5 weight percent neodymium, up to 100 ppm copper, and up to 175 ppm iron can result in high-melting-temperature NdMg intermetallics (e.g., NdMg cubic, cP2 CsCl type, melting point 800° C.; $NdMg_2$, cubic, cF24 $MgCu_2$ type, melting point 780° C.;) and low-melting-temperature intermetallic phases, such as aluminum containing intermetallic phases (e.g., $Mg_{17}Al_{12}$). Although additional processing of the cast alloy can refine the size and arrangement of the low-melting-temperature intermetallic phases and the grains of a first-phase (i.e., an alpha phase), the high-melting-temperature intermetallic phases (such as NdMg) can remain thermally unrefined in the solid state (e.g., resolutioned and precipitated as innocuous fine particles). Accordingly, the high-melting-temperature intermetallic phases can be considered permanently part of the alloy as long as it stays in the solid state. These permanent, high-melting-temperature, intermetallic precipitates can be formed when the cooling rate during solidification is slow enough that precipitation occurs prior to the solidification of the phases containing primarily low-melting-temperature elements; e.g., Mg-rich alpha phase.

Figure 4A:
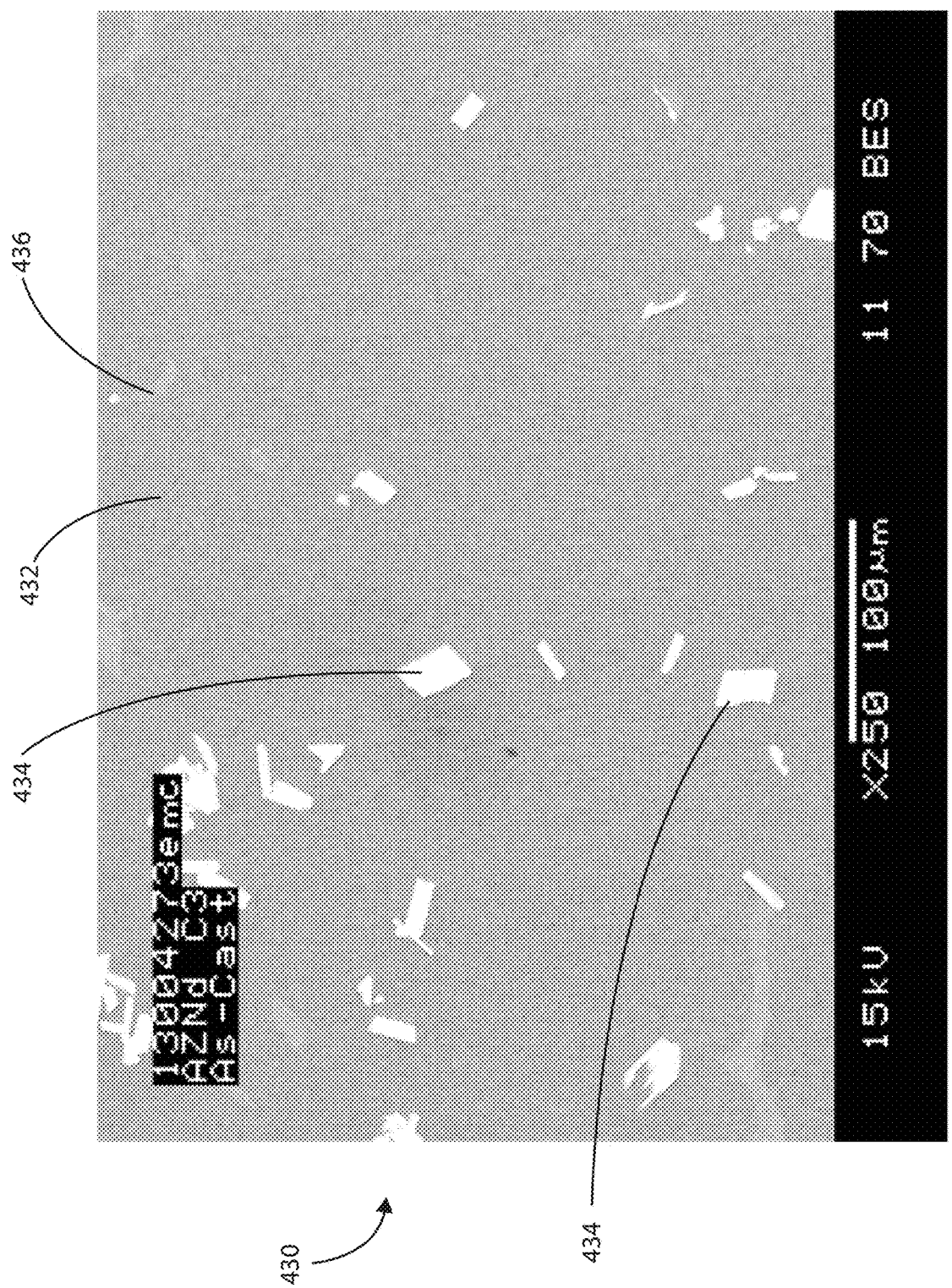
FIG. 4A depicts comparison microstructures.

FIG. 4A depicts a microstructure 430 that can result from the relatively slow cooling rate when using a mold, during a casting process, having no mold cooling apparatus on an alloy including at least 85 weight percent magnesium, between 5 and 11 weight percent aluminum, between 0.1 and 3 weight percent zinc, and between 0.05 and 0.3 weight percent manganese, between 0.6 and 1.5 weight percent neodymium, up to 100 ppm copper, and up to 175 ppm iron. As shown, permanent, high-melting-temperature, intermetallic phases (white) 434 are included within the alpha phase matrix (darker grey) 432. Non-permanent, low-melting-temperature, intermetallic phases (lighter gray) 436 can also be seen in the alpha phase matrix (darker grey) 432. As shown, permanent, high-melting-temperature, intermetallic phases 434 can be large. Additionally, permanent, high-melting-temperature, intermetallic phases 434 can be highly cathodic, and thus facilitate localized galvanic corrosion, material erosion, loss of material mechanical integrity, fracture at the localized corrosion sites, and ultimately early loss of mechanical integrity of the surgical implant. Without this localized corrosion and fracture event, the implant would corrode and lose mass more consistently throughout the surface of the implant, and would lose mechanical integrity at a more consistent and longer duration of time after implantation. Accordingly, in some cases, microstructures provided herein can limit the size, distribution, and amount of permanent, high-melting-temperature, intermetallic phases, improving the uniformity of surface erosion and improving stent degradation rate consistency.

Figure 4B:
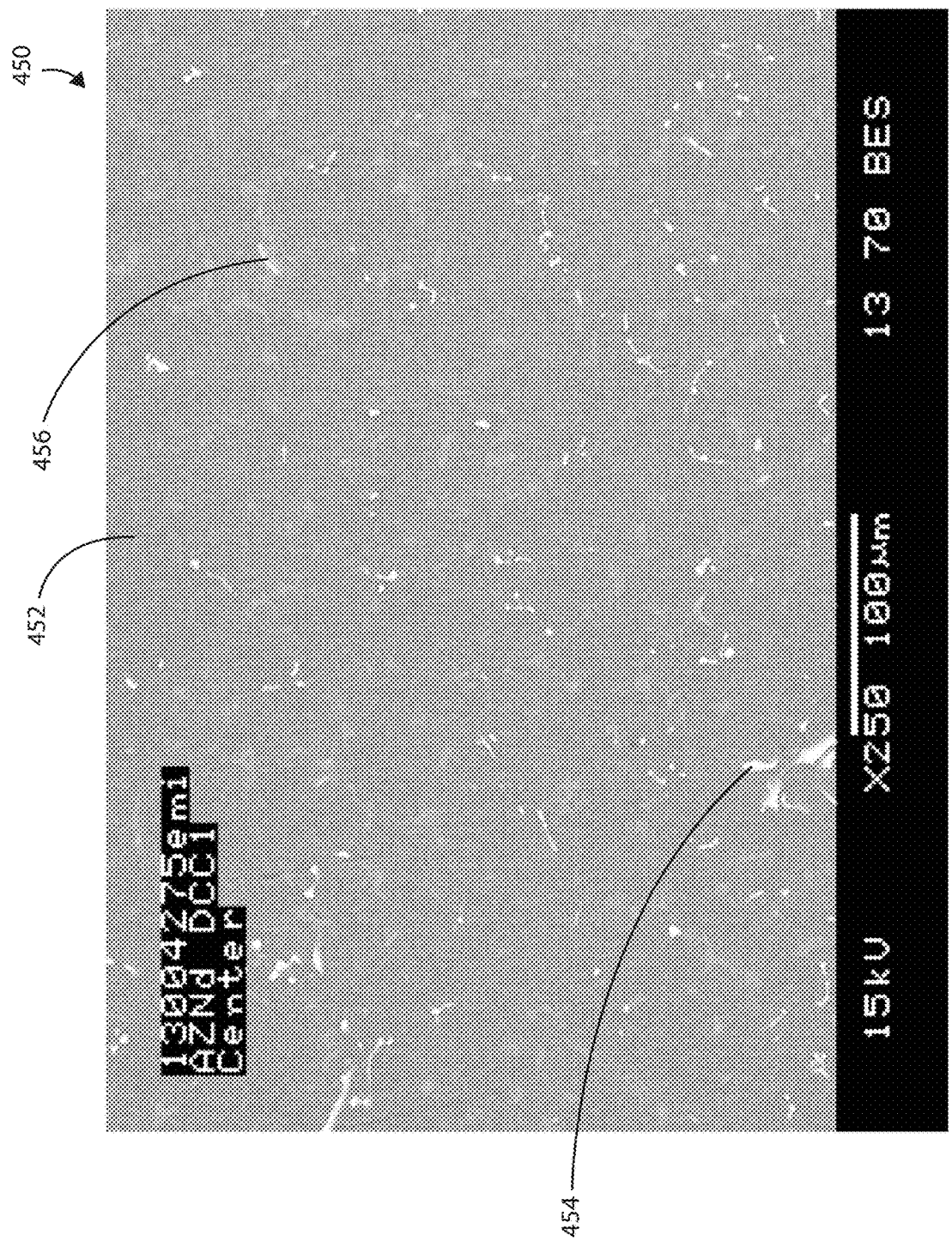
FIG. 4B depicts comparison microstructures.

FIG. 4B depicts a microstructure 450 that can be produced from a relatively faster cooling rate achieved from using direct-chill casting processes on an alloy including at least 85 weight percent magnesium, between 5 and 11 weight percent aluminum, between 0.1 and 3 weight percent zinc, and between 0.05 and 0.3 weight percent manganese, between 0.6 and 1.5 weight percent neodymium, up to 100 ppm copper, and up to 175 ppm iron. As shown, permanent, high-melting-temperature, intermetallic phases (white) 454 are included within the alpha phase matrix (darker grey) 452, but are smaller than the permanent, high-melting-temperature, intermetallic phases (white) 434 depicted in FIG. 4A. Non-permanent, low-melting-temperature, intermetallic phases (lighter gray) 456 can also be seen in the alpha phase matrix (darker grey) 452. The faster cooling rate during solidification achieved when using a direct chill casting process resulted in delaying some of the solidification of the high-melting-temperature elements. As a result, the solidification of some of the high-melting-temperature elements occurred when the solidification of the low-melting-temperature elements was occurring.

In some cases, microstructures provided herein can have permanent high-melting-temperature intermetallic compounds or phases that are relatively small compared to microstructures resulting from rather slow cooling. Faster cooling can result in fewer high-melting-temperature particles, and in high-melting-temperature particles that have an average longest dimension of 0.5 microns or less (or 0.00002 inches or less). In some cases, microstructures provided herein can have permanent, high-melting-temperature, intermetallic phases that have an average longest dimension of 0.1 microns or less (or 0.00004 inches or less), 0.05 microns or less (or 0.000002 inches or less), 0.01 microns or less (or 0.0000004 inches or less), or 0.005 microns or less (or 0.0000002 inches or less). In some cases, phases located along grain boundaries between first-phase grains can include a combination of permanent, high-melting-temperature, intermetallic phases and low-melting-temperature intermetallic phases. In some cases, microstructures provided herein can have less than 1 percent by volume (as determined by viewing the bioerodible body under 100-500× magnification on a metallography plane and calculating the area of different phases) of permanent, high-melting-temperature, intermetallic phases. In some cases, microstructures provided herein can have less than 0.5 percent by volume, less than 0.1 percent by volume, or less than 0.05 percent by volume of permanent, high-melting-temperature, intermetallic phases. In some cases, microstructures provided herein can have no visually resolvable volume of permanent, high-melting-temperature, intermetallic phases when viewing the bioerodible body under 200-500× magnification on an unetched metallography plane.

Figure 2:
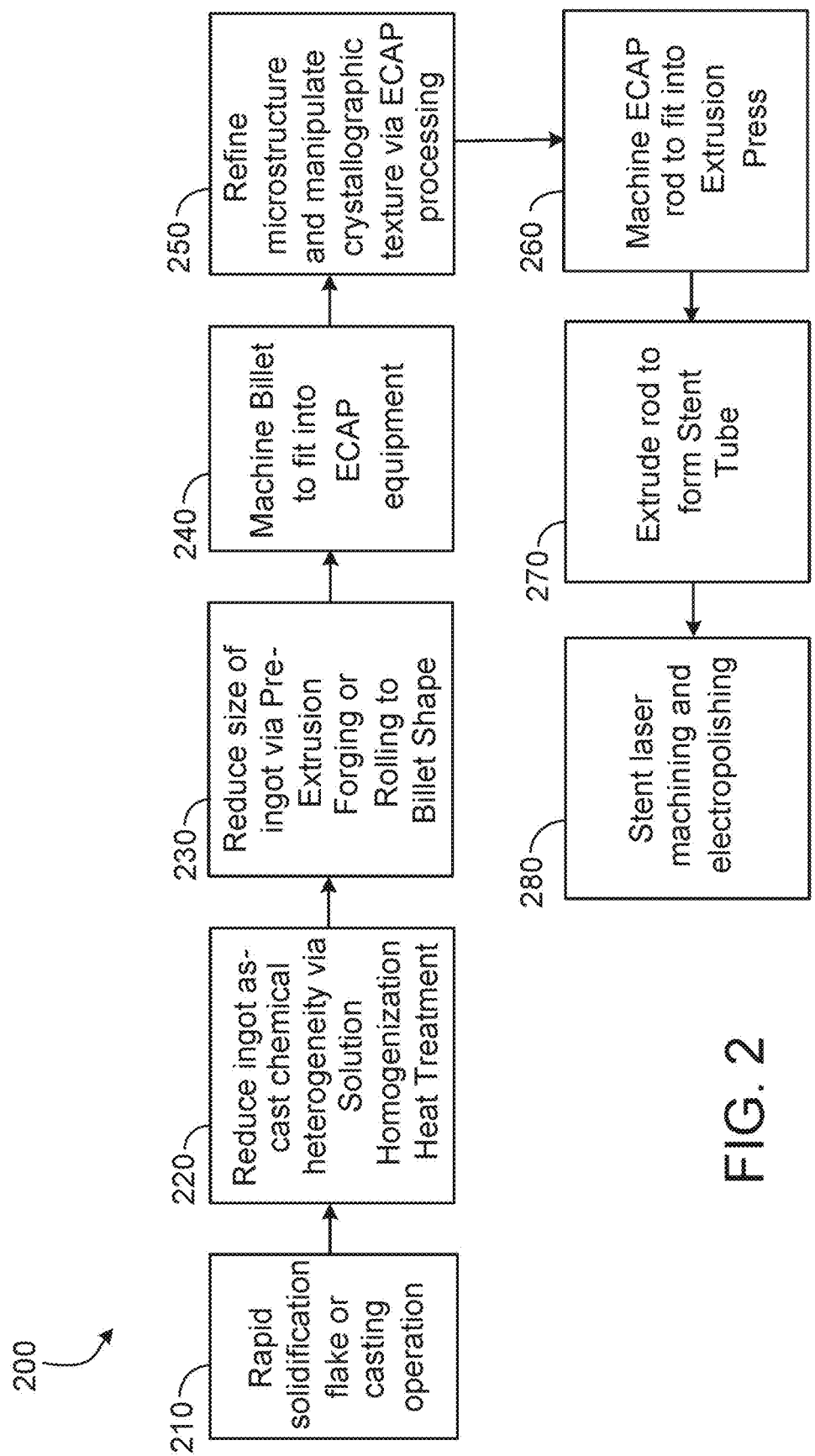
FIG. 2 is a flow chart of an exemplary method of forming a bioerodible body (e.g., a bioerodible stent body) provided herein.

Referring to FIG. 2, a process 200 of producing a bioerodible body having a microstructure provided herein can include a rapid solidification 210 of a solution of magnesium and one or more high-melting-temperature elements. In some cases, rapid solidification 210 can be a rapid solidification flake forming process. In some cases, rapid solidification 210 can be a rapid solidification casting operation. As used herein, "rapid solidification" means that the temperature of the fully liquid metal solution including at least magnesium and at least one high-melting-temperature element is reduced at a rate of at least 3.0° C./second down to a melting temperature of pure magnesium or the liquidus temperature of an alloy of Mg and low-melting-temperature elements. In some cases, rapid solidification processes used in processes provided herein reduce the temperature at a rate of at least 10° C./second, at least 30° C./second, at least 60° C./second, at least 100° C./second, at least 200° C./second, or at least 300° C./second. In some cases, the temperature of the solution is reduced from a temperature of at least 1000° C. to a temperature below 600° C. at a rate of at least 10° C./second. In some cases, the temperature of the solution is reduced from a temperature of at least 1100° C. to a temperature below 550° C. at a rate of at least 30° C./second. In some cases, rapid solidification 210 can establish a homogeneous distribution of the one or more high-melting-temperature elements and other elements in the solution on an atomic length scale that goes well beyond the solubility limit of ingot metallurgy, thereby creating a supersaturation of the alloying element in the magnesium matrix. Representative examples of suitable rapid solidification processes include melt spinning, planar flow casting, and laser beam surface melting. Other examples include vapor phase processes such as vapor deposition, plasma sputtering, and magnetron sputtering. Further examples include pulsed laser deposition and nanocluster deposition. Specific examples are described in the aforementioned U.S. Pat. No. 6,908,516 to Hehmann et al., which is hereby incorporated by reference.

In some cases, rapid solidification processing can produce fine grain microstructure, e.g., 1 micron (or 0.00004 inches) or less average alpha grain size. If a rapid solidification process produces alpha grain size that is larger than desired for the final product, solid state grain refinement processing can be performed. After rapid solidification 210, a microstructure of the rapidly solidified metal can be refined using one or more grain refinement techniques that occur at temperatures below the melting temperature of magnesium. In some cases, rapid solidification 210 can include techniques that produce flakes, which can be consolidated into an ingot, which can be further processed to produce a microstructure provided herein.

Figure 6:
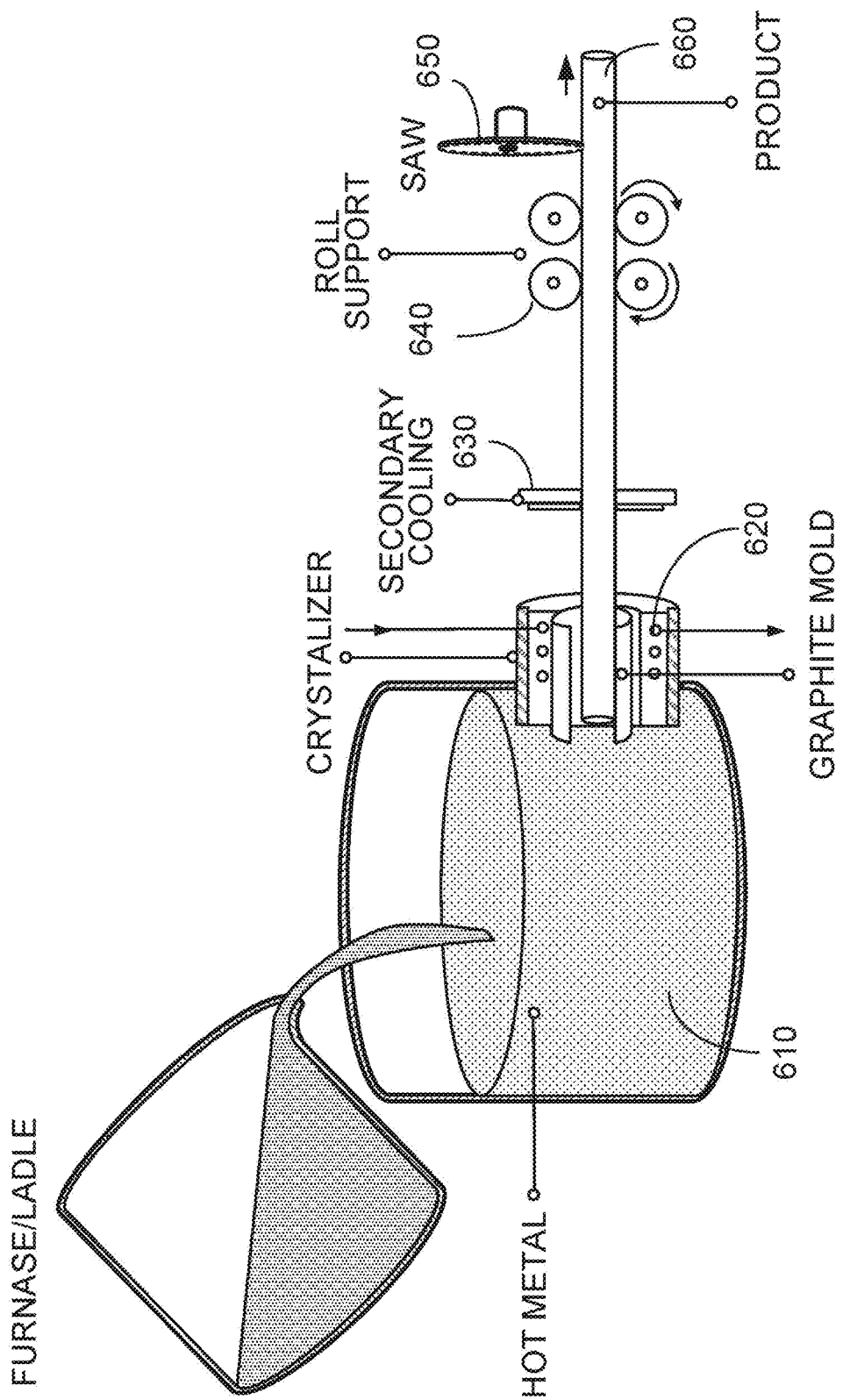
FIG. 6 depicts a horizontal continuous casting process, which can be used in methods provided herein to produce supersaturated magnesium alloys.

In some cases, rapid solidification 210 can directly cast an ingot. For example, FIG. 6 depicts a horizontal continuous casting process that can continuously cast a wire with rapid solidification. As shown, a hot melt 610 can be extruded through a heat exchanger/crystallizer 620 to rapidly cool the hot melt 610 from a temperature where the alloy is fully liquid 610 to a temperature of less than 650° C. at a rate of at least 3.0° C./second. Secondary cooler 630 can further reduce the temperature to a temperature of less than 450° C. Roll supporters 640 can support the material and/or pull the material during the extrusion. A saw 650 can conform the rod or tube 660 to desired dimensions. In some cases, tube or rod 660 can be wound into a tube and consolidated into a billet.

The microstructure provided herein can be formed by the following material treatments: (a) rapid solidification of a liquid solution of magnesium and one or more alloying elements; and (b) thermomechanical deformation of the solidified material to produce a microstructure provided herein. Processes provided herein can optionally include solid state heat treatments to homogenize the composition material, either before or after rapid solidification. Processes provided herein can optionally include processes for consolidating and/or shaping rapidly solidified alloy for thermomechanical deformation and/or shaping the magnesium alloy material after thermomechanical deformation into a bioerodible body for an endoprosthesis. FIG. 2 depicts a specific example of a process of forming a stent having a microstructure provided herein is depicted in.

As shown in FIG. 2, rapidly solidified flake or cast material can be heat treated in a solid state thermal exposure process 220 to solutionize low-melting-temperature intermetallic phases in an alpha matrix at a temperature below the melting point of magnesium. In some cases, rapid solidification 210 can include techniques that produce alloy flakes, which can be consolidated with solid state processing into a form such as a rod or billet before or after homogenization 220. In some cases, homogenization 220 can be implemented prior to rapid solidification. For example, in some cases a commercially purchased conventionally cast ingot can be homogenized prior to converting the homogenized cast ingot into metallic flake using rapid solidification 210. In some cases, homogenization 220 can heat an ingot or metallic flake at a temperature below the melting temperature of magnesium but greater than 300° C. for a period of at least 1 hour. In some cases, an ingot or metallic flake can be homogenized at a temperature of between 350° C. and 600° C. for a period of at least 3 hours, at a temperature of between 400° C. and 500° C. for a period of at least 6 hours, at a temperature of between 420° C. and 450° C. for a period of at least 12 hours, or at a temperature of 425° C. for at least 24 hours. In some cases, a follow-on solution treatment can be used if the homogenization treatment cooling was not controlled sufficiently to tailor the solid state low-melting-temperature second-phase precipitate size and location. In some cases, the ingot or billet is cooled rapidly after holding the ingot or billet at the elevated temperature in order to form relatively fine non-permanent, second-phase precipitates. For example, the ingot or billet can be cooled from the elevated hold temperature via forced gas cooling or liquid quenching. The ingot or billet can be homogenized in an inert atmosphere (e.g., in an argon atmosphere) or open atmosphere so long as surface oxides are removed. In some cases, the ingot or billet provided herein can be homogenized at a temperature of between 400° C. and 450° C. In some cases, the ingot or billet is held at a temperature of between 400° C. and 450° C. for at least 2 hours, at least 3 hours, or at least 4 hours. In some cases, the hold time at an elevated temperature is between 4 hours and 24 hours. For example, a bioerodible magnesium alloy ingot having a diameter of about 15 centimeters, or about 5.9 inches, can be heated to a temperature of 440° C. for 6 hours to homogenize the ingot, followed by quenching the ingot in a cooled argon gas stream.

Referring to FIG. 2, a homogenized magnesium can be forged or rolled 230 into a billet. In some cases, flake can be forged into a billet by cold compacting the flake and subject the green compact to extrusion. In some cases, cold compaction of the flakes can compact the flake to approximately 80% of the theoretical density of the magnesium by compressing it and degassing it for at least 1 hour under a vacuum of $10^{-2}$ Torr at a temperature of 350° C. After cold compaction, the compact can then be extruded or rolled to form a desired billet shape. In some cases, billet can be forged by powder metallurgy (solid-processing) into a magnesium flake.

In some cases, a homogenized casting can be extruded through a die or rolled to a desired diameter. After forging and rolling, beta phase precipitates can form within the alpha matrix (i.e., the supersaturated first-phase matrix). In some cases, the magnesium material can include aluminum as an alloyed element and the beta phase precipitates can include aluminum (e.g., $Mg_{17}Al_{12}$).

A billet rolled or forged in process 230 can be dimensioned for one or more high-strain processes, such as Equal-Channel Angular Extrusion ("ECAE") and Equal-Channel Angular Pressing ("ECAP"), as discussed below. In some cases, a billet rolled or forged in process 230 can be machined 240 to fit ECAE or ECAP equipment. In some cases, the billet is converted into a rod or hollow tube. In some cases, the rod or hollow tube can have an outer diameter of between 1 centimeter and 6 centimeters, or of between 0.4 inches and 2.4 inches.

A billet can be subjected to one or more high-strain processes to refine the microstructure into a microstructure provided herein. In some cases, the high-strain process(es) can include one or more equal-channel, high-strain processes, such as process 250 in FIG. 2. Equal-channel, high-strain processes include Equal-Channel Angular Extrusion ("ECAE") and Equal-Channel Angular Pressing ("ECAP"). ECAE is an extrusion process that produces significant deformation strain without reducing the cross sectional area of the piece. ECAE can be accomplished by extruding the alloy (e.g., a billet of the alloy) around a corner. For example, a billet of a bioerodible magnesium alloy provided herein can be forced through a channel having a 90 degree angle. The cross section of the channel can be equal on entry and exit. The complex deformation of the metal as it flows around the corner can produce very high strains. Because the cross section can remain the same, the billet can be extruded multiple times with each pass introducing additional strain. With each ECAE process, the orientation of the billet can be changed to introduce strain along different planes. In some cases, an ECAE die can include multiple bends. For example, FIGS. 5A-5D depict a variety of ECAE dies.

A billet provided herein can be extruded through one or more ECEA dies (e.g., as depicted in FIGS. 5A-5D) at temperatures lower than a homogenization temperature. Multiple equal-channel, high-strain extrusions can be performed at subsequently lower temperatures. The equal-channel, high-strain processes can yield a fine grain size with low-melting-temperature intermetallic phases (which can include fine low-melting-temperature intermetallic phases and/or permanent high temperature intermetallics) that are primarily located along the grain boundaries. In some cases, the dynamic recrystallization of the grain refinement caused by successive equal-channel, high-strain extrusions at declining temperatures can introduce more strain into the material and result in finer grain sizes as compared to cold working and annealing steps. In some cases, a billet is subjected to at least two ECAE processes at two different sequentially-lower temperatures. In some cases, a billet is subjected to at least three ECAE processes at different sequentially-lower temperatures.

For example, a billet including a magnesium-aluminum-neodymium material can be processed through two ECAE processes, with the first ECAE process occurring at a higher temperature than the second ECAE process. Each process can occur through a simple ECAE die having a single 90° corner, such as that depicted in FIG. 5A. The first ECAE process can be conducted at a temperature of between 250° C. and 400° C. to allow good diffusion of aluminum to the grain boundaries where it can precipitate in the form of $Mg_{17}Al_{12}$ low-melting-temperature intermetallic phases.

The $Mg_{17}Al_{12}$ low-melting-temperature intermetallic phases can be spherical and can have a diameter of about 0.25 microns or less (or about 0.00001 inches or less). Other low-melting-temperature intermetallic phases can also move towards the grain boundaries and precipitate there, depending on the particular alloy composition. Any neodymium intermetallic precipitates can also migrate to a grain boundary, but supersaturated neodymium in the alpha phase (first-phase) can remain in the supersaturated solid state solution.

Figure 5A:
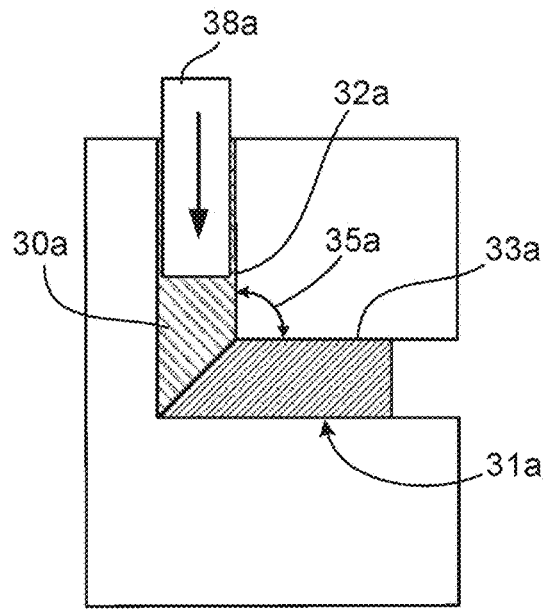
FIGS. 5A-5D depict exemplary Equal-Channel Angular Extrusion (ECAE) dies, which can be used in methods provided herein.

In the ECAE process shown in FIG. 5A, billet 30a is extruded through a channel 31a including two channel portions 32a, 33a of substantially identical cross-sectional areas having the respective centerlines thereof disposed at an angle 35a. As shown, angle 35a can be about 90°. In some cases, angle 35a can be between 45° and 170°, between 50° and 160°, between 60° and 135°, between 70° and 120°, between 80° and 100°, or between 85° and 95°. Billet 30a can have any appropriate cross section and be machined to provide a snug fit into entry channel portion 32a. In some cases, billet 30a can have a circular cross sectional shape. A ram 38a can force billet 30a through channel 31a using an appropriate extrusion ram pressure. The strain imposed on billet 30a is a function of angle 35a.

Figure 5B:
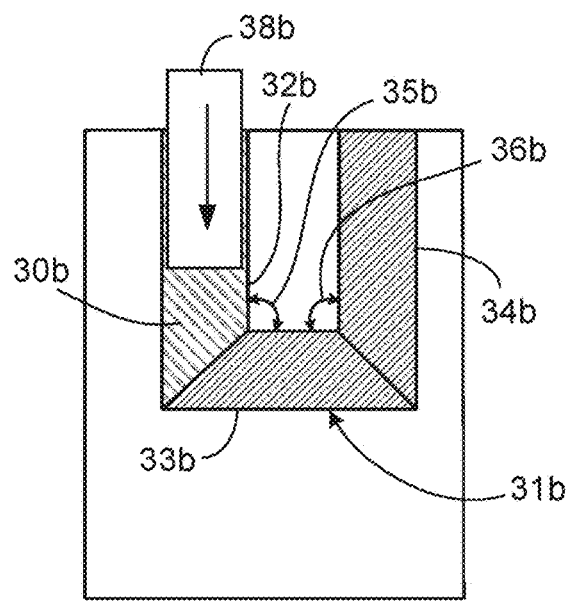

In the ECAE process shown in FIG. 5B, billet 30b is extruded through a channel 31b, including three channel portions 32b, 33b, and 34b of substantially identical cross-sectional areas having the respective centerlines thereof disposed at angles 35b and 36b. As shown, angles 35b and 36b can be about 90°. In some cases, angles 35b and 36b can be between 45° and 170°, between 50° and 160°, between 60° and 135°, between 70° and 120°, between 80° and 100°, or between 85° and 95°. Billet 30b can have any appropriate cross section and be machined to provide a snug fit into entry channel portion 32b. In some cases, billet 30b can have a circular cross sectional shape. In some cases, billet 30b can have a square cross-sectional shape. A ram 38b can force billet 30b through channel 31b using an appropriate extrusion ram pressure. The strain imposed on billet 30b is a function of angles 35b and 36b.

Figure 5C:
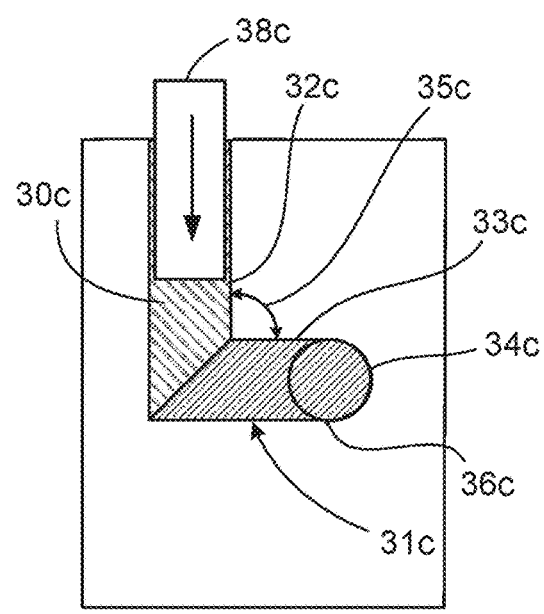

In the ECAE process shown in FIG. 5C, billet 30c is extruded through a channel 31c, including three channel portions 32c, 33c, and 34c of substantially identical cross-sectional areas having the respective centerlines thereof disposed at angles 35c and 36c. As shown, angles 35c and 36c can be about 90° and in separate planes. In some cases, angles 35c and 36c can be between 45° and 170°, between 50° and 160°, between 60° and 135°, between 70° and 120°, between 80° and 100°, or between 85° and 95°. Billet 30c can have any appropriate cross section and be machined to provide a snug fit into entry channel portion 32c. As shown, billet 30c can have a circular cross sectional shape. A ram 38c can force billet 30c through channel 31c using an appropriate extrusion ram pressure. The strain imposed on billet 30c is a function of angles 35c and 36c. Moreover, having the channel portions 32c, 33c, and 34c in different planes can impart shear forces along different planes in a single pass.

Figure 5D:
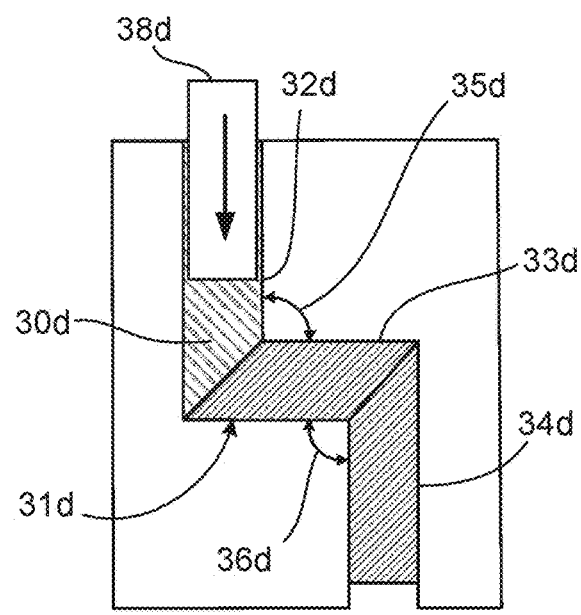

In the ECAE process shown in FIG. 5D, billet 30d is extruded through a channel 31d, including three channel portions 32d, 33d, and 34d of substantially identical cross-sectional areas having the respective centerlines thereof disposed at angles 35d and 36d. As shown, angles 35d and 36d can be about 90° and in opposite directions. In some cases, angles 35d and 36d can be between 45° and 170°, between 50° and 160°, between 60° and 135°, between 70° and 120°, between 80° and 100°, or between 85° and 95°. Billet 30d can have any appropriate cross section and can be machined to provide a snug fit into entry channel portion 32d. For example, billet 30d can have a circular cross sectional shape. A ram 38d can force billet 30d through channel 31d using an appropriate extrusion ram pressure. The strain imposed on billet 30d is a function of angles 35d and 36d.

Referring to FIG. 2, a billet coming out of the ECAE die can then optionally be machined to dimensions 260 needed for a rod extrusion step 270. Rod extrusion step 270 can form a rod or hollow tube having a reduced outer diameter after one or more high-strain processes. Tube or rod drawing from the billet can occur in multiple steps, with optional intermediate and final annealing steps, to reduce the diameter. The drawing and annealing processes can be controlled to preserve the microstructure formed in the one or more high-strain processes. In some cases, the material is annealed at a temperature of less than 300° C. In some cases, the material is annealed at a temperature of between 150° C. and 300° C., between 150° C. and 250° C., or between 150° C. and 200° C. Annealing steps can be used to allow the material to recover with limited recrystallization and prevent grain growth or changes in low-melting-temperature precipitate volume fraction and morphology. Annealing steps can also maintain a homogenous dispersion of low-melting-temperature intermetallic phases at the grain boundaries.

Individual stent bodies can be cut, e.g., cutting fenestrations between stent struts, using any suitable technique, and/or electropolished, as shown by step 280 in FIG. 2. For example, the fenestrations can be cut using a laser. In the case of a stent, a hollow tube having a bioerodible body having a microstructure provided herein can be further reduced in diameter and cut to form individual stent bodies that include fenestrations between stent struts. In some cases, the stent struts can have a width to thickness ratio of less than 1.2. In some cases, the thickness of the hollow tube and the stent struts can be between 80 microns and 160 microns (or between 0.0031 inches and 0.0024 inches).

A tubular body (e.g., stent tubing material) made from AZNd alloy of the formulation shown in Table 3 and having a microstructure provided herein can have an elastic modulus of between 39 and 44 GPa, a 0.2% Offset Yield Strength of between 150 and 350 MPa, an ultimate tensile strength of between 225 and 400 MPa, a tensile reduction in area (RIA) of between 30% and 80%. In some cases, stent tubing material provided herein can have a tensile RIA of between 45% and 80%. In some cases, stent tubing material provided herein can maintain its initial elastic modulus, yield strength, ultimate tensile strength, and a tensile RIA within ±10% following storage for 180 days at a temperature of between 20° C. and 25° C. and a relative humidity of less than 30%.

Bioerodible magnesium alloys having a microstructure provided herein can be polished, such as in step 280, to have a smooth surface finish. In some cases, an endoprosthesis provided herein can have a surface including a bioerodible magnesium alloy having a surface roughness $R_a$ of less than 0.5 microns (or 0.00002 inches), less than 0.4 microns (or 0.00002 inches), less than 0.3 microns (or 0.0001 inches), or less than 0.2 microns (or 0.000008 inches). Bioerodible magnesium alloys having microstructure provided herein can have improved corrosion resistance, which can provide a slower bioerosion rate. A stent body of a bioerodible magnesium alloy having a microstructure provided herein can have an in-vitro corrosion rate (e.g., penetration rate) of less than 200 μm per year (or 16.67 μm per month) after a period of 28 days of continuous immersion in non-flowing, agitated Simulated Body Fluid (agitated at 60 rpm) at 37° C. where the Simulated Body Fluid ("SBF") is present in an amount of at least 10 times the initial volume of a endoprosthesis material, e.g., a stent material. The in-vitro corrosion rate can be measured as a distance normal to the surface that has degraded. The ingredients of the SBF, which are added to water, are shown in Table 3.

TABLE 3

SBF Ingredients

| Chemical | Mass/Volume |
| --- | --- |
| NaCl | 5.403 g |
| $NaHCO_3$ | 0.504 g |
| $Na_2CO_3$ | 0.426 g |
| KCl | 0.225 g |
| $K_2HPO_4 \cdot 3H_2O$ | 0.230 g |
| $MgCl_2 \cdot 6H_2O$ | 0.311 g |
| 0.2M NaOH | 100 mL |
| HEPES | 17.892 g |
| $CaCl_2$ | 0.293 g |
| $Na_2SO_4$ | 0.072 g |

A coating can be applied over a bioerodible body of an endoprosthesis provided herein. For example, a stent provided herein can include a stent body formed of a bioerodible magnesium alloy including a microstructure provided herein and a coating overlying the surface of the stent body. A coating can slow or delay the initial degradation of the bioerodible magnesium alloy upon placement within a physiological environment by serving as a temporary barrier between the Mg alloy and the environment. For example, delaying the bioerosion processes can allow the body passageway to heal and a stent to become endothelialized (surrounded by tissues cells of the lumen wall) before the strength of the stent is reduced to a point where the stent fails under the loads associated with residing within a body lumen (e.g., within a blood vessel). When stent fragments are endothelialized, the segments of the stent can be contained by the lumen wall tissue and are thus less likely to be released into the blood stream. Endothelialization can also block the oxygen-rich turbulent flow of the blood stream from contacting the endoprosthesis, thus further reducing the erosion rate of the endoprosthesis. In some cases, a stent provided herein can include a coating that includes titanium oxide, aluminum oxide, or a combination thereof. Examples of suitable coatings can be found in U.S. Patent Application Publication No. 2012/0059455, which is hereby incorporate by reference in its entirety, particularly the sections describing coatings formed by atomic layer deposition.

The stent can optionally include a therapeutic agent. In some cases, the coating can include a therapeutic agent. In some cases, the coating can include a polymer (e.g., a bioerodible polymer). For example, a drug-eluting polymeric coating can be applied to the stent body provided herein. In some cases, a stent provided herein can be essentially polymer-free (allowing for the presence of any small amounts of polymeric materials that may have been introduced incidentally during the manufacturing process such that someone of ordinary skill in the art would nevertheless consider the coating to be free of any polymeric material). The therapeutic agent may be any pharmaceutically acceptable agent (such as a drug), a biomolecule, a small molecule, or cells. Exemplary drugs include antiproliferative agents such as paclitaxel, sirolimus (rapamycin), tacrolimus, everolimus, biolimus, and zotarolimus. Exemplary biomolecules include peptides, polypeptides and proteins; antibodies; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Exemplary small molecules include hormones, nucleotides, amino acids, sugars, lipids, and compounds have a molecular weight of less than 100 kD. Exemplary cells include stem cells, progenitor cells, endothelial cells, adult cardiomyocytes, and smooth muscle cells.

A stent provided herein can include one or more imaging markers. Imaging markers can assist a physician with the placement of the stent. Imaging markers can be radiopaque marks to permit X-ray visualization of the stent.

Stent 20 can be configured for vascular, e.g., coronary and peripheral vasculature or non-vascular lumens. For example, it can be configured for use in the esophagus or the prostate. Other lumens include biliary lumens, hepatic lumens, pancreatic lumens, and urethral lumens.

Stent 20 can be of a desired shape and size (e.g., coronary stents, aortic stents, peripheral vascular stents, gastrointestinal stents, urology stents, tracheal/bronchial stents, and neurology stents). Depending on the application, the stent can have a diameter of between about 1 millimeter (mm) to about 46 mm, or between about 0.04 inches to about 1.8 inches, for example. In certain embodiments, a coronary stent can have an expanded diameter ranging from about 2 mm to about 6 mm, or from about 0.08 inches to about 0.24 inches. In some cases, a peripheral stent can have an expanded diameter ranging from about 4 mm to about 24 mm, or from about 0.16 inches to about 0.94 inches. In certain embodiments, a gastrointestinal and/or urology stent can have an expanded diameter ranging from about 6 mm to about 30 mm, or from about 0.24 inches to about 1.18 inches. In some cases, a neurology stent can have an expanded diameter ranging from about 1 mm to about 12 mm, or from about 0.04 inches to about 0.47 inches. An abdominal aortic aneurysm (AAA) stent and a thoracic aortic aneurysm (TAA) stent can have a diameter ranging from about 20 mm to about 46 mm, or from about 0.79 inches to about 1.81 inches. The stent can be balloon-expandable, self-expandable, or a combination of both (e.g., see U.S. Pat. No. 6,290,721).

Non-limiting examples of additional endoprostheses that can include a bioerodible magnesium alloy including a microstructure provided herein include stent grafts, heart valves, and artificial hearts. Such endoprostheses are implanted or otherwise used in body structures, cavities, or lumens such as the vasculature, gastrointestinal tract, abdomen, peritoneum, airways, esophagus, trachea, colon, rectum, biliary tract, urinary tract, prostate, brain, spine, lung, liver, heart, skeletal muscle, kidney, bladder, intestines, stomach, pancreas, ovary, uterus, cartilage, eye, bone, joints, and the like.

All publications, patent applications, patents, and other references mentioned herein are incorporated by reference herein in their entirety.

Still further embodiments are within the scope of the following claims.

What is claimed is:

1. A bioerodible endoprosthesis comprising:
    a bioerodible body comprising an alloy comprising at least 85 weight percent magnesium and at least one high-melting-temperature element having a melting temperature of greater than 700° C., the alloy having a microstructure comprising equiaxed magnesium-rich phase grains and high-melting-temperature intermetallic phases, the equiaxed magnesium-rich phase grains having an average grain diameter of less than or equal to 10 microns and the high-melting-temperature intermetallic phases comprising at least 20 weight percent of the at least one high-melting-temperature elements and having an average longest dimension of 3 microns or less;

wherein the bioerodible body is created by performing at least one high-strain process on an ingot or a billet at a temperature from 250 degrees C. to 400 degrees C. and an intermediate annealing step at a temperature from 150 degrees C. to 250 degrees C. to form the microstructure comprising the equiaxed magnesium-rich phase grains and the high-melting-temperature intermetallic phases; and wherein the alloy of the bioerodible body is formed by rapid solidifying, prior to performing the at least one high-strain process on an ingot or a billet, by cooling the alloy to a temperature of 650 degrees C. or less at a rate of at least 3.0 degrees C. per second to form a cast alloy.

2. The endoprosthesis of claim 1, wherein the at least one high-melting-temperature element is a rare earth metal.

3. The endoprosthesis of claim 1, wherein the at least one high-melting-temperature element has a melting temperature of at least 1,000° C.

4. The endoprosthesis of claim 1, wherein the at least one high-melting-temperature element is selected from the group consisting of neodymium, tin, yttrium, cerium, lanthanum, and gadolinium.

5. The endoprosthesis of claim 1, wherein the alloy comprises between 0.5 and 5.0 weight percent of the at least one high-melting-temperature element.

6. The endoprosthesis of claim 1, wherein the high-melting-temperature intermetallic phases are primarily centered upon grain boundaries between equiaxed magnesium-rich phase grains and do not extend into an interior of the equiaxed magnesium-rich phase grains by more than 0.3 microns from a grain boundary when viewed at 200-500× magnification on a metallography plane.

7. The endoprosthesis of claim 1, wherein the alloy further comprises aluminum, zinc, manganese, or a combination thereof.

8. The endoprosthesis of claim 7, wherein the microstructure further comprises low-melting-temperature intermetallic phases having an average longest dimension of 1 micron or less, the low-melting-temperature intermetallic phases comprising aluminum, zinc, manganese, or a combination thereof.

9. The endoprosthesis of claim 8, wherein the low-melting-temperature intermetallic phases comprise $Mg_{17}Al_{12}$.

10. The endoprosthesis of claim 1, wherein the alloy has an elastic modulus of between 39 GPa and 44 GPa, a 0.2% offset yield strength of between 150 MPa and 350 MPa, an ultimate tensile strength of between 250 MPa and 400 MPa, and a tensile reduction in area of at least 30%.

11. The endoprosthesis of claim 1, wherein the alloy maintains an initial elastic modulus, yield strength, ultimate tensile strength, and a tensile RIA within +/−10% following storage for 180 days at a temperature of between 20° C. and 25° C. and a relative humidity of less than 30%.

12. The endoprosthesis of claim 11, wherein the bioerodible body comprises between 5 and 11 weight percent aluminum, between 0.1 and 3.0 weight percent zinc, up to 0.3 weight percent manganese, and between 0.6 and 1.5 weight percent neodymium, and balance magnesium.

13. The endoprosthesis of claim 1, wherein the endoprosthesis is a stent comprising a plurality of struts, wherein the struts have a width to thickness ratio of less than 1.2.

14. The endoprosthesis of claim 1, wherein the rate of cooling the alloy to a temperature of 650 degrees C. or less is at least 30 degrees C. per second to form the cast alloy.

* * * * *